US007232929B2

(12) United States Patent
Bialer et al.

(10) Patent No.: US 7,232,929 B2
(45) Date of Patent: Jun. 19, 2007

(54) AMIDE DERIVATIVES OF 2,2,3,3-TETRAMETHYLCYCLOPROPANE CARBOXYLIC ACID

(75) Inventors: Meir Bialer, Jerusalem (IL); Boris Yagen, Jerusalem (IL); Eyal Sobol, Rosh Ha Ayin (IL); Dan Kaufmann, Netanya (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 10/547,299

(22) PCT Filed: Feb. 15, 2004

(86) PCT No.: PCT/IL2004/000193

§ 371 (c)(1),
(2), (4) Date: Aug. 29, 2005

(87) PCT Pub. No.: WO2004/076432

PCT Pub. Date: Sep. 10, 2004

(65) Prior Publication Data

US 2006/0148861 A1 Jul. 6, 2006

(30) Foreign Application Priority Data

Feb. 28, 2003 (IL) ....................................... 154694
Sep. 4, 2003 (IL) ....................................... 157751

(51) Int. Cl.
*C07C 307/02* (2006.01)
*A61K 31/18* (2006.01)

(52) U.S. Cl. ............................ 564/86; 564/44; 564/57; 560/312; 548/142; 514/363; 514/507; 514/575; 514/594; 514/603

(58) Field of Classification Search ................ 514/363, 514/603, 575, 594, 507; 564/44, 57, 86; 560/312; 548/142

See application file for complete search history.

(56) References Cited

U.S. PATENT DOCUMENTS

| | | | |
|---|---|---|---|
| 5,585,358 A | 12/1996 | Bialer et al. | |
| 5,880,157 A | 3/1999 | Sterling et al. | |
| 6,323,365 B1 | 11/2001 | Blaler et al. | |
| 6,417,399 B1 | 7/2002 | Bialer et al. | |
| 6,555,585 B2 | 4/2003 | Shirvan et al. | |
| 6,630,602 B1 | 10/2003 | Bialer et al. | |
| 6,958,416 B2 | 10/2005 | Bialer et al. | |
| 6,969,732 B2 | 11/2005 | Bialer et al. | |
| 2002/0052418 A1 | 5/2002 | Shirvan et al. | |
| 2002/0115718 A1 | 8/2002 | Chen et al. | |
| 2004/0204495 A1 | 10/2004 | Shirvan et al. | |

FOREIGN PATENT DOCUMENTS

| WO | 95/09835 A1 | 4/1995 |
|---|---|---|
| WO | 95/21814 A1 | 8/1995 |
| WO | 98/30536 A1 | 7/1998 |
| WO | 99/48859 A1 | 9/1999 |
| WO | 99/54282 A1 | 10/1999 |
| WO | 03/064374 A1 | 8/2003 |
| WO | 2004/105746 A1 | 12/2004 |
| WO | 2005/009430 A1 | 2/2005 |
| ZA | 7400202 A | 11/1974 |

OTHER PUBLICATIONS

Gao et al, J. Med Chem, 1995, vol. 38, pp. 2292-2301.*
Agam, G., et al., "Myo-inositol-1-phosphate (MIP) Synthase: A Possible New Target for Antibipolar Drugs", Bipolar Disorders (2002), pp. 15-20, Suppl. 1.
Bialer, M., et al., "New Antiepileptic Drugs Currently in Clinical Trials: Is There a Strategy in Their Development?", Therapeutic Drug Monitoring (2002), pp. 85-90, vol. 24, No. 1.
Bialer, M., et al., "Pharmacokinetic Analysis and Antiepileptic Activity of Tetra-Methylcyclopropane Analogues of Valpromide", Pharmaceutical Research (1996), pp. 284-289, vol. 13, No. 2.
Bialer, M., et al., "Pharmacokinetic Consideration in the Design of Better and Safer New Antiepileptic Drugs", Journal of Controlled Release (1999), pp. 187-192, vol. 62.
Bialer, M., et al., "Pharmacokinetic of a Valpromide Isomer, Valnoctamide, in Healthy Subjects", European Journal of Clinical Pharmacology (1990), pp. 289-291, vol. 38.
Blotnik, S., et al., "Disposition of Two Tetramethylcyclopropane Analogues of Valpromide in the Brain, Liver, Plasma and Urine of Rats", European Journal of Pharmaceutical Sciences (1998), pp. 93-98, vol. 6.
Gao, J., et al., "Increasing Binding Constants of Ligands to Carbonic Anhydrase by Using Greasy Tails", Journal of Medicinal Chemistry (1995), pp. 2292-2301, vol. 38, No. 13.
Greenberg, M., et al., "Inhibition of Myo-Inositol-Phosphate Synthase by Valproate; a Mechanism for Mood Stabilization?", European Neuropsychopharmacology (2003), pp. S107-S108, vol. 13, Supplement 4.
Huber, A., et al., "Siezure Suppression by Adenosine A2A Receptor Activation in a Rat Model of Audiogenic Brainstem Epilepsy", Neuroscience Letters (2002), pp. 289-292, vol. 329.
Isoherranen, N., et al., "Anticonvulsant Profile and Teratogenicity of N-methyl-tetramethylcyclopropyl Carboxamide: A new Antiepileptic Drug", EPILEPSY (2002), pp. 115-126, vol. 43.
Isoherranen, N., et al., "New CNS-active Drugs Which are Second-Generation Valproic Acid: Can They Lead to the Development of Magic Bullet?", Current Opinion in Neurology (2003), pp. 203-211, vol. 16.
Malhotra, J. et al., "Effect of Adenosine Receptor Modulation on Pentylenetetrazole-Induced Seizures in Rats", British Journal of Pharmacology (1997), pp. 282-288, vol. 120.
Sheen, K., et al., "Signs of Neuropathic Pain Depend on Signals From Injured Nerve Fibers in a Rat Model", Brain Research (1993), pp. 62-68, vol. 610.

(Continued)

*Primary Examiner*—Shailendra Kumar
(74) *Attorney, Agent, or Firm*—Browdy and Neimark, PLLC

(57) ABSTRACT

The invention relates to new 2,2,3,3-tetramethylcyclopropane carboxamide derivative compounds, pharmaceutical compositions thereof and uses thereof for treating psychotic disorders, neurodegenerative diseases, epilepsy and pain.

25 Claims, 2 Drawing Sheets

OTHER PUBLICATIONS

Shuto, S., et al., "Synthesis and Biological Activity of Conformationally Restricted Analogs of Milnacipran: (1S, 2R)-1-Phenyl-2-U(S)-1-Aminopropyl-N,N-Diethylcyclopropanecarboxamide, An Efficient Noncompetitive N-methyl-D-aspartic acid receptor antagonist", Journal of Medicinal Chemistry (1996), pp. 4844-4852, vol. 39.

Shuto, S., et al. "(Plus or minus)-(z)-2-(aminomethyl)-1-phenylcyclopropanecarboxamide Derivatives as a New Prototype of NMDA Receptor Antagonists", Journal of Medicinal Chemistry (1995), pp. 2964-2968, vol. 38.

Spiegelstein, O., et al., "Enantioselective Synthesis and Teratogenicity of Propylisopropyl Acetamide, a CNS Active Chiral Amide Analogue of Valproic Acid", CHIRALITY (1999), pp. 645-650, vol. 11.

White, H.S., et al., "General principles-Discovery and Preclinical Development of Antiepileptic Drugs", Antiepileptic Drugs (2002), 5th edition, RH Levy, RH Mattson, BS Meldrum, E Perucca (eds), Lippincott William & Wilkins, Philadelphia, pp. 36-48.

* cited by examiner

AMIDE DERIVATIVES OF 2,2,3,3-TETRAMETHYLCYCLOPROPANE CARBOXYLIC ACID

This application is a 371 of PCT/IL04/00193, filed Feb. 15, 2004.

FIELD OF THE INVENTION

The invention relates to new amide derivatives of 2,2,3,3-tetramethylcyclopropane carboxylic acid, pharmaceutical compositions comprising them as well as uses thereof.

BACKGROUND OF THE INVENTION

Four major antiepileptic drugs (AEDs) are used for the treatment of epilepsy (epileptic seizures and convulsions): phenytoin, carbamazepine, phenobarbital and valproic acid (VPA). However, about 25% of the patients do not respond to the current medications. Furthermore, AEDs are administered repetitively as chronic treatment and the adverse effects associated with antiepileptic therapy are of a major concern. The major established AEDs are associated with some rare but severe side effect such as teratogenicity. In addition, all the AEDs have other adverse effects that limit their use. Valproic acid itself has considerable adverse effects including fatal hepatotoxicity.

One approach to obtain improved antiepileptic agents has been to prepare the primary amide derivatives of valproic acid and its analogs. Valnoctamide (VCD) and propylisoproylacetamide (PID) are analogous of the amide derivative of valproic acid, valpromide (VPD). They have improved anticonvulsant activity when compared to VPA. These amide analogues of valproic acid have been shown to be non-teratogenic, O. Spiegelstein, M. Bialer, M. Radatz, H. Nau and B. Yagen Chirality, 11:645–650 (1999).

Amide derivatives of tetramethylcyclopropane carboxylic acid have also been previously evaluated for their anticonvulsant activity (M. Bialer, S. Hadad, B. Kadry, A. Abdul-Hai, A. Haj-Yehia, J. Sterling, Y. Herzig and B. Yagen Pharm Res. 13:284–289 (1996); J. Sterling, et al. U.S. Pat. No. 5,880,157, issued March. 1999; N. Isoherranen et al, Epilepsy 43: 115–126 (2002)). These derivatives had good anticonvulsant activity and superior brain penetration than VPA. The N-methyl-tetramethylcyclopropyl carboxamide has a wide spectrum of anticonvulsant activity and is approximately 10 times more potent than VPA in animal models of epilepsy. In addition, N-methyl-tetramethylcyclopropane carboxamide and tetramethylcyclopropane carboxamide were not teratogenic in mouse model.

Currently 25% of epileptic patients are not seizure free with existing medications and thus are considered as therapy resistant or refractory epileptic patients.

Thus, there is still a substantial need for new anti epileptic and central nervous system (CNS) drugs that will be effective in refractory epileptic patients.

Furthermore, an urgent need still exists in the art for anti epileptic agents with an improved efficacy and a wider margin between the dose which is therapeutic and that which is neurotoxic.

Additionally, it would be highly advantageous to have new compounds effective against pain, psychotic disorders and neurodegenerative diseases.

SUMMARY OF THE INVENTION

According to one aspect of the present invention there is provided a 2,2,3,3-tetramethylcyclopropane carboxamide derivative compound of formula I:

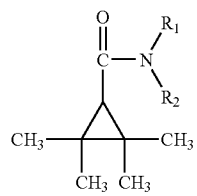

[I]

including enantiomers, hydrates, solvates and pharmaceutically acceptable salts thereof, wherein,
$R_1$ is hydrogen or $C_1$–$C_6$alkyl group and
$R_2$ is selected from:
(a) a member having the structural formula:

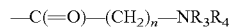
—C(=O)—(CH$_2$)$_n$—NR$_3$R$_4$ wherein n=0–6, $R_3$ and $R_4$ are the same or different and are independently selected from hydrogen, $C_1$–$C_6$alkyl group, an acyl group having the formula RC(=O)—, wherein R is a $C_1$–$C_6$alkyl group, and a keto group having the formula RC(=O)R'—, wherein R and R' are $C_1$–$C_6$alkyl groups which may be the same or different;
(b) a $C_1$–$C_6$alkyl sulfonamide group;
(c) an (N—$C_1$–$C_6$alkyl)$C_1$–$C_6$alkyl sulfonamide group;
(d) an aryl sulfonamide group;
(e) a $C_1$–$C_6$alkyl aryl sulfonamide group,
(f) a thiadiazole sulfonamide group;
(g) a $C_1$–$C_6$alkyl-thiadiazole sulfonamide group;
(h) an (N—$C_1$–$C_6$alkyl)aryl sulfonamide group;
(i) an (N—$C_1$–$C_6$alkyl)$C_1$–$C_6$alkyl aryl sulfonamide group;
(j) an (N—$C_1$–$C_6$alkyl)thiadiazole sulfonamide group;
(k) an (N—$C_1$–$C_6$alkyl)$C_1$–$C_6$alkyl-thiadiazole sulfonamide group; and
(l) a $C_1$–$C_6$alkoxy group.

According to another aspect of the present invention there is provided a pharmaceutical composition comprising as an active ingredient a therapeutically effective amount of at least one compound as defined in the present invention and a pharmaceutically acceptable carrier.

According to yet another aspect of the present invention there is provided a pharmaceutical composition for the treatment of psychotic disorders, neurodegenerative diseases, epilepsy and pain comprising as an active ingredient a therapeutically effective amount of at least one compound as defined in the present invention and a pharmaceutically acceptable carrier.

According to an additional aspect of the present invention there is provided use of the compounds as defined in the present invention in the preparation of a medicament for treating a disease selected from: psychotic disorders, neurodegenerative diseases, epilepsy and pain.

According to yet additional aspect of the present invention there is provided a method of preventing, treating or ameliorating a medical condition selected from psychotic disorders, neurodegenerative diseases, epilepsy and pain, in a mammal in need of such treatment comprising administering to the mammal an effective amount of the compound as defined in the present invention, sufficient to prevent, treat or ameliorate the effect of said medical condition.

BRIEF DESCRIPTION TO DRAWINGS

DETAILED DESCRIPTION OF THE INVENTION

Figure 1:
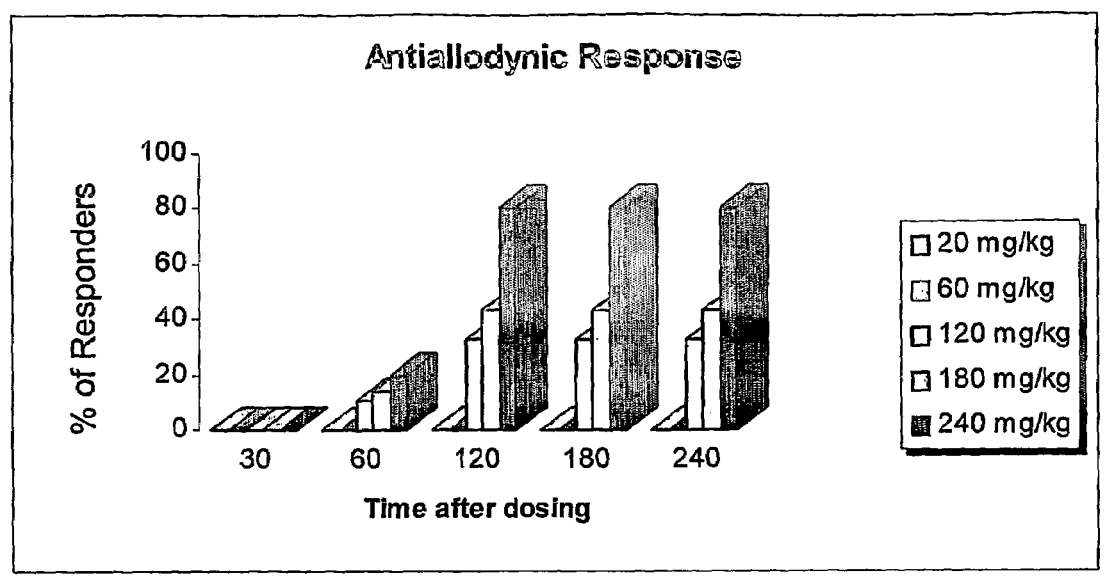
FIG. 1 illustrates the allodynic response presented as percent absolute responders in the von frey filaments (VFF) testing.

The present invention relates to a 2,2,3,3-tetramethylcyclopropane carboxamide derivative compound of formula I:

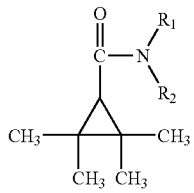

[I]

including enantiomers, hydrates, solvates and pharmaceutically acceptable salts thereof,
wherein,
$R_1$ is hydrogen or $C_1$–$C_6$ alkyl group and
$R_2$ is selected from:
(a) a member having the structural formula:

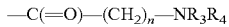

—C(═O)—(CH$_2$)$_n$—NR$_3$R$_4$ wherein n=0–6, $R_3$ and $R_4$ are the same or different and are independently selected from hydrogen, $C_1$–$C_6$alkyl group, an acyl group having the formula RC(═O)—, wherein R is a $C_1$–$C_6$ alkyl group, and a keto group having the formula RC(═O)R'—, wherein R and R' are $C_1$–$C_6$ alkyl groups which may be the same or different;
(b) a $C_1$–$C_6$alkyl sulfonamide group;
(c) an (N—$C_1$–$C_6$alkyl)$C_1$–$C_6$alkyl sulfonamide group;
(d) an aryl sulfonamide group;
(e) a $C_1$–$C_6$alkyl aryl sulfonamide group,
(f) a thiadiazole sulfonamide group;
(g) a $C_1$–$C_6$alkyl-thiadiazole sulfonamide group;
(h) an (N—$C_1$–$C_6$alkyl)aryl sulfonamide group;
(i) an (N—$C_1$–$C_6$alkyl)$C_1$–$C_6$alkyl aryl sulfonamide group;
(j) an (N—$C_1$–$C_6$alkyl)thiadiazole sulfonamide group;
(k) an (N—$C_1$–$C_6$alkyl)$C_1$–$C_6$alkyl-thiadiazole sulfonamide group; and
(l) a $C_1$–$C_6$alkoxy group.

It should be noted that the present invention excludes the 2,2,3,3-tetramethylcyclopropane carboxamide derivative compounds disclosed in references as follows: M. Bialer, S. Hadad, B. Kadry, A. Abdul-Hai, A. Haj-Yehia, J. Sterling, Y. Herzig and B. Yagen Pharm Res. 13:284–289 (1996); J. Sterling, et al. U.S. Pat. No. 5,880,157 (issued March. 1999); N. Isoherranen et al, Epilepsia 43: 115–126 (2002); WO 03/064374 (PCT/IL02/01050), the disclosures of these references are incorporated herein by reference in their entirety.

As used herein the group —C(═O)— (or —CO—) refers to a carbonyl group having the formula

As used herein the group —S(═O)$_2$— (or —SO$_2$—) refers to a sulfonyl group having the formula

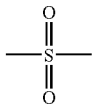

As used herein the term "$C_1$–$C_6$alkyl" when used alone or in combination with other groups refers to a saturated aliphatic hydrocarbon of 1 to 6 carbon atoms. The $C_1$–$C_6$alkyl may be a straight or a branched alkyl. The $C_1$–$C_6$alkyl group may be for example methyl, ethyl, propyl, isopropyl, butyl, isobutyl, tertiary butyl, sec-butyl, amyl, pentyl, isopentyl, hexyl.

Preferably the alkyl consists of 1–3 carbon atoms and most preferably the alkyl is a methyl.

The alkyl group may be at the terminal position of the compound or may be in a non-terminal position of the compound where it is attached at 2 different non-terminal carbon atoms to the flanking other groups (in this case the alkyl refers to alkylene containing from 1 to 6 carbon atoms such as methylene, ethylene, propylene, isopropylene, butylene, isobutylene, tert-butylene, sec-butylene and the like).

For example the R' of the keto group having the formula RC(═O)R'— refers to a $C_1$–$C_6$alkyl group (an alkelene) having for example the structure —(CH$_2$)$_n$— where n=1–6.

Whenever a numerical range e.g. "1–6" is stated herein, it means that the group in this case the alkyl group, may contain 1 carbon atom, 2 carbon atoms, 3 carbon atoms, etc., up to and including 6 carbon atoms.

Unless otherwise specified, whenever the term 'alkyl' is used in the present invention it refers to a $C_1$–$C_6$alkyl.

The term "$C_1$–$C_6$alkyl sulfonamide" as used herein refers to —(CH$_2$)$_n$S(═O)$_2$NH$_2$, where n=1–6.

The term "N—$C_1$–$C_6$alkyl" as used herein refers to the N-monoalkyl or N-dialkyl group of the corresponding compound. Preferably the N—$C_1$–$C_6$alkyl is the N-methyl or N-dimethyl group.

The term "(N—$C_1$–$C_6$alkyl)$C_1$–$C_6$alkyl sulfonamide" as used herein refers to —(CH$_2$)$_n$S(═O)$_2$NR$_3$R$_4$ where n=1–6, $R_3$ and $R_4$ are independently selected from the group consisting of hydrogen and $C_1$–$C_6$ alkyl, excluding the case where $R_3$=$R_4$=H.

The term "aryl sulfonamide" as used herein refers to -Aryl-S(═O)$_2$NH$_2$.

The term "aryl" in the aryl sulfonamide defined above, refers to an aromatic ring for example a phenyl.

The sulfonamide group may be attached in the meta, ortho or para position of the aromatic ring.

The aryl sulfonamide group may be further substituted.

When substituted, the aryl sulfonamide group may be substituted with one or more, more preferably one, two or three, most preferably one or two substituents, preferably halo group.

The term "halo" refers to fluoro, chloro, bromo, or iodo, preferably to chloro.

Preferably the substituted aryl sulfonamide is substituted phenyl sulfonamide

Preferably the substituted aryl sulfonamide is chlorobenzenesulfonamide shown below.

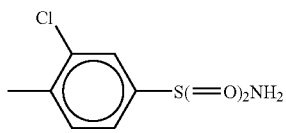

The term "(N—$C_1$–$C_6$alkyl)aryl sulfonamide" as used herein refers to -Aryl-S(=O)$_2$NR$_3$R$_4$, where R$_3$ and R$_4$ are independently selected from the group consisting of hydrogen and $C_1$–$C_6$ alkyl, excluding the case where R$_3$=R$_4$=H.

Preferably the aryl is a phenyl.

The aryl may be further substituted.

The term "$C_1$–$C_6$alkyl aryl sulfonamide" refers to —(CH$_2$)$_n$-Aryl-S(=O)$_2$NH$_2$, where n=1–6, preferably n=1–3 and most preferably n=2.

The sulfonamide group may be attached in the meta, ortho or para position of the aromatic ring.

Preferably the aryl group is a phenyl.

The aryl of the aryl sulfonamide may be further substituted.

Preferably the $C_1$–$C_6$alkyl aryl sulfonamide is ethylbenzenesulfonamide:

The term "(N—$C_1$–$C_6$alkyl)$C_1$–$C_6$alkyl aryl sulfonamide" refers to —(CH$_2$)$_n$-Aryl-S(=O)$_2$NR$_3$R$_4$, where n=1–6, R$_3$ and R$_4$ are independently selected from the group consisting of hydrogen and $C_1$–$C_6$ alkyl, excluding the case where R$_3$=R$_4$=H.

Preferably the aryl group is a phenyl.

The aryl of the aryl sulfonamide may be further substituted.

An example for "thiadiazole sulfonamide" is

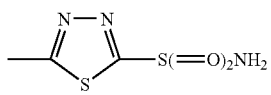

(1,3,4-thiadiazole-2-sulfonamide)

An example for "$C_1$–$C_6$alkyl-thiadiazole sulfonamide" is

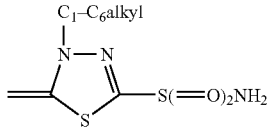

($C_1$–$C_6$-C4-alkyl-$\Delta^2$-1,3,4-thiadiazole-2-sulfonamide)

An example for "(N—$C_1$–$C_6$alkyl)thiadiazole sulfonamide" is

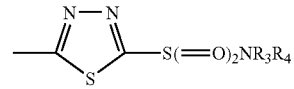

((N—$C_1$–$C_6$alkyl)-1,3,4-thiadiazole-2-sulfonamide)

where R$_3$ and R$_4$ are independently selected from the group consisting of hydrogen and $C_1$–$C_6$ alkyl, excluding the case where R$_3$=R$_4$=H.

An example for "(N—$C_1$–$C_6$alkyl)$C_1$–$C_6$alkyl-thiadiazole sulfonamide" is

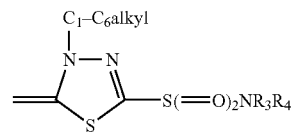

((N—$C_1$–$C_6$alkyl)$C_1$–$C_6$-4-alkyl-$\Delta^2$-1,3,4-thiadiazole-2-sulfonamide)

where R$_3$ and R$_4$ are independently selected from the group consisting of hydrogen and $C_1$–$C_6$ alkyl, excluding the case where R$_3$=R$_4$=H.

The term "$C_1$–$C_6$alkoxy" as used herein refers to —O—$C_1$–$C_6$alkyl where $C_1$–$C_6$alkyl is a straight or branched saturated aliphatic hydrocarbon of 1 to 6 carbon atoms.

According to a preferred embodiment of the present invention, R$_1$ in the derivative compounds of structure formula I is hydrogen.

Further according to a preferred embodiment of the present invention, the alkyl group of R$_1$ is a straight or branched chain.

Still further according to a preferred embodiment of the present invention, any alkyl group or alkoxy group of R$_2$ is a straight or branched chain.

For example: the $C_1$–$C_6$alkyl group of the $C_1$–$C_6$alkyl sulfonamide group; (N—$C_1$–$C_6$alkyl)$C_1$–$C_6$alkyl sulfonamide group; $C_1$–$C_6$alkyl aryl sulfonamide group; $C_1$–$C_6$alkyl-thiadiazole sulfonamide group; (N—$C_1$–$C_6$alkyl)aryl sulfonamide group; (N—$C_1$–$C_6$alkyl) thiadiazole sulfonamide group; (N—$C_1$–$C_6$alkyl) $C_1$–$C_6$alkyl-thiadiazole sulfonamide group; and the $C_1$–$C_6$alkoxy group may be a straight or branched chain.

Additionally according to a preferred embodiment of the present invention, n in the structural formula —C(=O)—(CH$_2$)$_n$—NR$_3$R$_4$ is zero.

In this case where n=0, R$_2$ is an amide having the structural formula —C(=O)—NR$_3$R$_4$ wherein, R$_3$ and R$_4$ are the same or different and are independently selected from hydrogen, $C_1$–$C_6$alkyl group, an acyl group having the formula RC(=O)—, wherein R is a $C_1$–$C_6$alkyl group, and a keto group having the formula RC(=O)R'—, wherein R and R' are $C_1$–$C_6$alkyl groups which may be the same or different.

Further according to a preferred embodiment of the present invention, R$_1$ is hydrogen or $C_1$–$C_6$ alkyl group and R$_2$ is a member having the structure formula: —C(=O)—(CH$_2$)$_n$—NR$_3$R$_4$ wherein n=0, $R_3$ and $R_4$ are the same or different and independently selected from hydrogen and $C_1$–$C_6$alkyl group.

According to this preferred embodiment $R_2$ is an amide having the formula —C(=O)—$NR_3R_4$.

Moreover according to a more preferred embodiment of the present invention, $R_1$, $R_3$ and $R_4$ are hydrogen. In this case the compound is N-2,2,3,3-tetramethylcyclopropanecarbonyl urea.

Further according to a more preferred embodiment of the present invention, at one of $R_1$, $R_3$ or $R_4$ is a methyl.

Examples of compounds where at least one of $R_1$, $R_3$ or $R_4$ is a methyl are 1,1-N,N-dimethyl-2,2,3,3-tetramethylcyclopropanecarbonyl urea and 1,3-N,N-dimethyl-2,2,3,3-tetramethylcyclopropanecarbonyl urea;

According to additional preferred embodiment of the present invention $R_2$ is an amide group having the structure formula: —C(=O)—$NR_3R_4$ wherein $R_3$ or $R_4$ is hydrogen and the other of $R_3$ or $R_4$ is selected from an acyl group having the formula RC(=O)—, wherein R is a $C_1$–$C_6$alkyl group, and a keto group having the formula RC(=O)R'—, wherein R and R' are $C_1$–$C_6$alkyl groups which may be the same or different.

More preferably $R_3$ or $R_4$ is an acyl group having the formula RC(=O)— wherein R is a $C_1$–$C_6$alkyl group.

More preferably $R_1$ is hydrogen and $R_3$ or $R_4$ of the amide group of $R_2$ defined above is hydrogen and the other of $R_3$ or $R_4$ is an acyl group having the formula RC(=O)— wherein R is a $C_1$–$C_6$alkyl group, Most preferably the R of the acyl group described above is a methyl (In this case the compound is: N-acetyl-2,2,3,3-tetramethylcyclopropanecarbonyl urea).

According to another preferred embodiment of the present invention, the $R_2$ of the derivative compounds of formula I is $C_1$–$C_6$alkoxy group.

According to another more preferred embodiment of the present invention, $R_1$ is hydrogen and the $R_2$ is $C_1$–$C_6$alkoxy group.

According to another still more preferred embodiment of the present invention, the $C_1$–$C_6$alkoxy group is methoxy.

Example of a compound where $C_1$–$C_6$alkoxy group is methoxy is N-methoxy-2,2,3,3-tetramethylcyclopropane carboxamide.

Additionally according to a preferred embodiment of the present invention, $R_2$ of the derivatives of formula I is thiadiazole sulfonamide group.

Moreover according to a more preferred embodiment of the present invention, $R_1$ is hydrogen and the $R_2$ is thiadiazole sulfonamide group. Example of a preferred compound is 5-2,2,3,3-tetramethylcyclopropanecarbonylamido-1,3,4-thiadiazole-2-sulfonamide.

According to an additional preferred embodiment of the present invention, $R_2$ of the derivative compounds of formula I is $C_1$–$C_6$alkyl-thiadiazole sulfonamide group.

According to an additional more preferred embodiment of the present invention, $R_1$ is hydrogen and $R_2$ is $C_1$–$C_6$alkyl-thiadiazole sulfonamide group.

According to an additional still more preferred embodiment of the present invention, $R_1$ is hydrogen and $R_2$ is methyl thiadiazole sulfonamide group. A preferred compound according to this embodiment is 5-2,2,3,3-tetramethylcyclopropanecarbonylamido-4-methyl-$\Delta^2$-1,3,4-thiadiazole-2-sulfonamide.

Further according to a preferred embodiment of the present invention, $R_2$ of formula I is aryl sulfonamide group.

Still further according to a more preferred embodiment of the present invention $R_1$ is hydrogen and $R_2$ is aryl sulfonamide group.

Still further according to a more preferred embodiment of the present invention, the aryl sulfonamide group is a phenyl sulfonamide group.

Example of compounds according to this preferred embodiment are:

2,2,3,3-tetramethylcyclopropanecarbonylamidobenzene-o-sulfonamide, 2,2,3,3-tetramethylcyclopropanecarbonylamidobenzene-m-sulfonamide, or 2,2,3,3-tetramethylcyclopropanecarbonylamidobenzene-p-sulfonamide.

According to a preferred embodiment of the present invention the derivative compounds are selected from:

N-2,2,3,3-tetramethylcyclopropanecarbonyl urea;

1,1-N,N-dimethyl-2,2,3,3-tetramethylcyclopropanecarbonyl urea;

1,3-N,N-dimethyl-2,2,3,3-tetramethylcyclopropanecarbonyl urea;

N-acetyl-2,2,3,3-tetramethylcyclopropanecarbonyl urea;

N-methoxy-2,2,3,3-tetramethylcyclopropane carboxamide;

5-2,2,3,3-tetramethylcyclopropanecarbonylamido-1,3,4-thiadiazole-2-sulfonamide;

5-2,2,3,3-tetramethylcyclopropanecarbonylamido-4-methyl-$\Delta^2$-1,3,4-thiadiazole-2-sulfonamide;

N-2,2,3,3,-tetramethylcyclopropanecarbonyl-taurinamide;

2,2,3,3-tetramethylcyclopropanecarbonylamidobenzene-o-sulfonamide;

2,2,3,3-tetramethylcyclopropanecarbonylamidobenzene-m-sulfonamide; and 2,2,3,3-tetramethylcyclopropanecarbonylamidobenzene-p-sulfonamide.

According to a more preferred embodiment of the present invention the derivative is N-2,2,3,3-tetramethylcyclopropanecarbonyl urea.

Some of the compounds of the present invention may posses chiral centers. Both the racemic mixtures and the specific stereoisomes in their isolated or essentially isolated forms are within the scope of the present invention.

The above compounds are presented in the table below:

| Compound Number | Structure | Chemical Name |
|---|---|---|
| I | 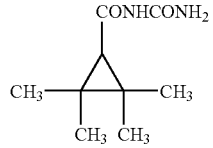 | N-2,2,3,3-tetramethylcyclopropane carbonyl urea |

-continued

| Compound Number | Structure | Chemical Name |
|---|---|---|
| II | 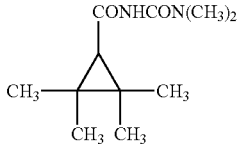 | 1,1-N,N-dimethyl-2,2,3,3-tetramethylcyclo propanecarbonyl urea |
| III | 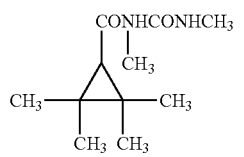 | 1,3-N,N-dimethyl-2,2,3,3-tetramethylcyclopropane carbonyl urea |
| IV | 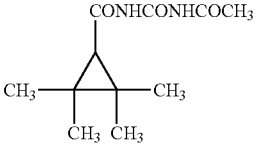 | N-acetyl-2,2,3,3-tetramethylcyclo propanecarbonyl urea |
| V | 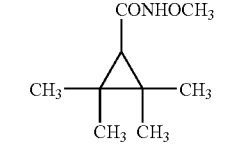 | N-methoxy-2,2,3,3-tetramethylcyclo propane carboxamide |
| VI | 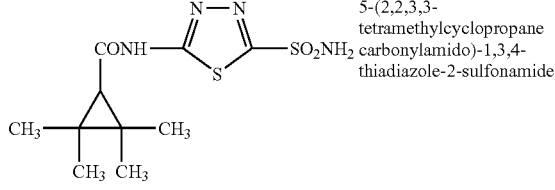 | 5-(2,2,3,3-tetramethylcyclopropane carbonylamido)-1,3,4-thiadiazole-2-sulfonamide |
| VII | 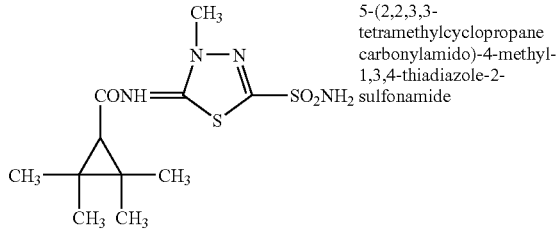 | 5-(2,2,3,3-tetramethylcyclopropane carbonylamido)-4-methyl-$\Delta^2$-1,3,4-thiadiazole-2-sulfonamide |
| VIII | 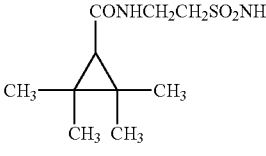 | N-2,2,3,3-tetramethylcyclopropane carbonyl-taurinamide |

-continued

| Compound Number | Structure | Chemical Name |
|---|---|---|
| IX–XI | (structure: cyclopropane with four CH₃ groups attached, connected via CONH to a benzene ring bearing SO₂NH₂) | 2,2,3,3-tetramethylcyclopropanecarbonylamidobenzene-o-sulfonamide (compound IX) 2,2,3,3-tetramethylcyclopropanecarbonylamidobenzene-m-sulfonamide (compound X) 2,2,3,3-tetramethylcyclopropanecarbonylamidobenzene-p-sulfonamide; (compound XI) |

A compound according to the present invention can be administered to a treated subject (mammal) per se, or in pharmaceutical composition where it is mixed with suitable pharmaceutically acceptable carriers (excipients).

The invention further provides a pharmaceutical composition comprising as an active ingredient a therapeutically effective amount of at least one compound as described in the present invention and a pharmaceutically acceptable carrier.

As used herein a "pharmaceutical composition" refers to a preparation of one or more compounds described herein, with other inert chemical components such as suitable pharmaceutically acceptable carriers. The purpose of a pharmaceutical composition is to facilitate administration of a compound to a mammal.

As used herein the term "pharmaceutically acceptable carrier" refers to an inert non-toxic carrier or diluent that does not cause significant irritation to a subject (mammal) and does not abrogate the biological activity and properties of the administered compound.

Examples without limitation of carriers are lactose, sucrose, water, organic solvents and polyethyleneglycol.

The carriers may include additional excipients such as binders, disintegrants, lubricants, surface active agents, preservatives and favoring agents.

Pharmaceutical compositions for use in the context of the present invention include compositions wherein the active ingredient is contained in an amount effective to achieve the intended purpose. More specifically, a therapeutically effective amount means an amount of a compound effective to prevent, alleviate or ameliorate one or more causes, complications or symptoms of a disease of the subject being treated.

According to a preferred embodiment of the present invention the route of administration of the composition is selected from oral, parenteral, inhalation, topical, transdermal, intranasal and rectal.

Additionally according to a preferred embodiment of the present invention the parenteral route of administration is selected from intravenous, intramuscular, intraperitoneal and subcutaneous administration.

Most preferred is the oral route of administration.

The pharmaceutical composition of the present invention may be formulated as to provide immediate release or sustained release of the active ingredient from the dosage form after administration to a patient by employing procedures well known in the art.

The final form of the composition includes but not limited to a liquid, a syrup, an elixir, an emulsion, a suspension, drops, a spray, a cream, an ointment, a lotion, a gel, a paste, a powder, a granule, a tablet, a caplet, a pill, a capsule, a suppository, a transdermal patch or an injection.

The pharmaceutically acceptable carrier selected for preparing the pharmaceutical compositions of the present invention depends on the final form of the composition.

Typically, such carriers include additional excipients such as binders, disintegrants, adsorbents, lubricants, wetting agents, buffering agents and surface active agents.

The pharmaceutical compositions of the present invention are preferably present in a unit dosage form. Unit dosage form as used herein refers to physically discrete units suited as unitary dosages for the mammalian subject to be treated, such as a tablet, a capsule, or powders in vials or ampoules, each unit containing a predetermined quantity of the active ingredient calculated to produce the desired therapeutic effect.

Preferably the pharmaceutical composition in a unit dosage form comprises a therapeutically effective amount of the active ingredient in an amount from 1 mg to 1000 mg, more preferably 10 to 500 mg and most preferably 20 to 200 mg.

Oral dosage forms of the present invention suitable for oral administration may be presented as discrete pharmaceutical unit dosage forms, such as capsules, cachets, soft elastic gelatin capsules, tablets, caplets, or aerosols sprays, each containing a predetermined amount of the active ingredients, as a powder or granules, or as a solution or a suspension in an aqueous liquid, a non-aqueous liquid, an oil-in-water emulsion, or a water-in-oil liquid emulsion. Dosage forms such as oil-in-water emulsions typically comprise surfactants such as an anionic surfactant, for example anionic phosphate ester or lauryl sulfates, but other types of surfactants such as cationic or nonionic surfactants may be used in the compositions of the present invention. See generally, Remington's Pharmaceutical Sciences, 18th ed., Mack Publishing, Easton Pa. (1990).

For the purpose of preparing a tablet dosage form, various pharmaceutical carriers which are well-known in this field can be widely used. As to the examples of carriers, excipients such as lactose, sodium chloride, glucose, starch, calcium carbonate, kaolin, cellulose, aluminum silicate and the like may be used; the binders may be for example water, ethanol, propanol, glucose solution, starch solution, gelatin solution, carboxymethyl cellulose, shellac, methyl cellulose, polyvinylpyrrolidone and the like; the disintegrants may be for example starch, sodium alginate, sodium laurylsulfate, sodium starch glycolate and the like; the wetting agents may be for example glycerin, surfactants and the like; the adsorbents may be for example starch, lactose, kaolin, bentonite, colloidal silicic acid and the like; lubricants such as talc, strearates, polyethylene glycols and the like can be used. The tablets preparations can be further shaped into tablets coated with usual tablet coating, for example sugar coated tablets, gelatin film coated tablets, tablets coated with enteric coating, tablets coated with film coating, or double layer tablets and multiple layer tablets.

For the purpose of preparing a capsule dosage form, the compounds of formula [I] as the active ingredients are mixed with the above-mentioned various carriers and the mixture or granules prepared from the mixtures are placed into rigid gelatin capsules or soft capsules.

For the purpose of preparing a suppository dosage form, various carriers which are well-known in this field can be widely used. As to the examples of carries, polyethylene glycols, cacao butter, higher alcohols, esters of higher alcohols, gelatin, semi-synthesized glycerides and the like can be mentioned.

For the purpose of preparing an injection dosage form, liquid preparations, emulsion preparations and suspension preparations are sterilized, further these preparations are preferably isotonic to the blood, and all the diluents which are conventionally used in this field can also be used for example, water, ethyl alcohol, macrogols, propylene glycol, ethyoxylated isostearyl alcohol, polyoxylated isostearyl alcohol and polyoxyethylenesorbitan fatty acid esters.

Additionally, for the purpose of preparing an isotonic injection solutions, an adequate amount of sodium chloride, glucose or glycerin may be added to the injection preparations, further, usual dissolving additives, buffering agents, preservatives and the like may be added.

An example of a pharmaceutical carrier for preparing an injection emulsion preparation is triglyceride emulsion. An example of an acceptable triglyceride emulsion useful in the intravenous and intraperitoneal administration of the compounds of the present invention is the triglyceride emulsion commercially distributed under the tradename Intralipid®.

Moreover, if necessary, coloring agents, preservatives, spices, flavors, sweetening agents and others may be added to the pharmaceutical preparations of the present invention.

Topical preparations such as creams, ointments, pastes, gels, lotions, transdermal patches, inhalants, sprays, aerosols and the like are formulated by using carriers and exipients which are well known in the field.

Methods of preparing the compositions of the present invention include the step of bringing into association a compound of the present invention with the pharmaceutical carrier. In general, the compositions are prepared by uniformly and intimately bringing into association a compound of the present invention with liquid, semi-solid or solid carriers, and then, if necessary, shaping the product.

The pharmaceutical compositions of the invention may be prepared by methods of pharmacy well known to those skilled in the art, e.g. by means of conventional mixing, dissolving, pulverizing, granulating, compressing, emulsifying, levigating, or lyophilizing processes. See generally, Remington's Pharmaceutical Sciences, 16$^{th}$ ed., Mack Publishing Company, Easton, Pa. (1980).

Pharmaceutical compositions for use in accordance with the present invention may thus be formulated in conventional manner using one or more pharmaceutically acceptable carriers comprising excipients and auxiliaries, which facilitate processing of the active compounds into preparations which, can be used pharmaceutically. The proper formulation is dependent upon the route of administration chosen.

The amount of the active ingredient that may be combined with the pharmaceutical carrier to produce a single dosage form will vary depending upon the mammal treated and the particular mode of administration.

For example, a composition intended for oral administration to humans may vary from about 5% to about 95% w/w of the total composition.

Dosage unit forms will generally contain between 1 to 1000 mg of the active ingredient, more preferably 10 to 500 mg and most preferably 20 to 200 mg.

As used herein the term "treating" includes abrogating, preventing, alleviating, slowing or reversing the progression of a disease, or substantially preventing the appearance of clinical symptoms of a disease.

As used herein the term "neurodegenerative disease" refers broadly to disorders or diseases that affect the nervous system and are characterized by gradual neuronal loss and/or gradual loss of neuronal function, including but are not limited to age-associated memory impairment, Parkinson's disease, Alzheimer's disease, Huntington's chorea disease and amyotrophic lateral sclerosis.

The degeneration may also be due to a trauma such as that following head injury or operation, due to lack of blood supply or oxygen (ischemia or hypoxia) following trauma, stroke or a disease process.

As used herein the term the term "pain" refers to all types of pain. Preferably the term "pain" refers to chronic pain, such as lower back pain; pain due to arthritis, e.g., osteoarthritis; joint pain, e.g., knee pain or carpal tunnel syndrome; myofascial pain; migraine; and neuropathic pain. The term "pain" further includes acute pain, such as pain associated with muscle strains and sprains; headaches; pain associated with surgery; or pain associated with various forms of tissue injury, e.g., inflammation, infection, and ischemia.

Most preferably this term concerns neuropathic pain or migraine.

As used herein the term the term "neuropathic pain" refers to any pain which initial cause was due to injury to the neural tissue whether the pain is experienced at or distal to the site of injury.

As used herein the term the term "migraine" refers to an often familial symptom complex of periodic attacks of vascular headache, usually temporal and unilateral in onset, commonly associated with irritability, nausea, vomiting, constipation or diarrhoea and often photophobia, attacks are preceded by constriction of the cranial arteries, usually with resultant prodromal sensory (especially ocular) symptoms and commence with the vasodilation that follows.

As used herein the term "psychotic disorder" refers to both acute and chronic conditions including schizophrenia, anxiety and related disorders (e.g. panic attack), depression and bipolar disorders.

Preferably the term concerns bipolar disorders.

As used herein the term the term "bipolar disease" refers to mood disorders characterized by a history of manic, mixed, or hypomanic episodes, usually with concurrent or previous history of one or more major depressive episodes, including bipolar I disorder, bipolar II disorder, and cyclothymic disorder. Cf. depressive d's. 2. a term sometimes used in the singular to denote either bipolar I d. or bipolar II d., or both.

By a most preferred embodiment the disease is epilepsy.

The present invention additionally relates to the use of the compounds as defined in the present invention in the preparation of a medicament for treating a disease selected from: psychotic disorders, neurodegenerative diseases, epilepsy and pain.

Preferably the psychotic disorder is selected from schizophrenia, anxiety, depression and bipolar disorder.

Preferably the neurodegenerative disease is selected from: age-associated memory impairment, Parkinson's disease, Alzheimer disease, Hungtinton's chorea disease and amyotropic lateral sclerosis.

In a preferred embodiment the pain is selected from neuropathic pain, chronic pain, headaches and migraine.

As used herein the term "mammal" refers to any member of the class Mammalia, including a human.

Preferably, the mammal herein is human.

The present invention additionally provides a method of preventing, treating, or ameliorating a medical condition selected from psychotic disorders, neurodegenerative diseases, epilepsy and pain, in a mammal in need of such treatment comprising administering to the mammal an effective amount of the compound as defined in the present invention, sufficient to prevent, treat or ameliorate the effect of the medical condition.

Preferably the psychotic disorder is selected from schizophrenia, anxiety, depression and bipolar disorder.

Preferably the neurodegenerative disease is selected from: age-associated memory impairment, Parkinson's disease, Alzheimer disease, Hungtinton's chorea disease and amyotropic lateral sclerosis.

In a preferred embodiment the pain is selected from neuropathic pain, chronic pain, headaches and migraine.

According to a preferred embodiment the mammal is a human

Thus, the pharmaceutical compositions of the present invention are useful for the treatment of psychotic disorders (such as schizophrenia, anxiety, depression or bipolar disorder, preferably bipolar disorder), neurodegenerative diseases (such as age-associated memory impairment, Parkinson's disease, Alzheimer disease, Hungtinton's chorea disease and amyotropic lateral sclerosis), epilepsy and pain (such as neuropathic pain, chronic pain, headaches and migraine).

The treatment may be prophylactic, for preventing the disease from occurring such as, for example, for preventing neuropathic pain following surgery by administration of the compound of the invention prior to surgery or for example for prevention of migraines, or epileptic seizures. Alternatively the administration may be performed after the disease or condition were already established so as to eliminate or decrease at least one of the manifestations of the disease or condition.

Preferably, the therapeutically or prophylactically effective amount of an active ingredient administered orally ranges from 1 mg to 1000 mg daily, more preferably from 10 mg to 500 mg daily and most preferably 20 to 200 mg, either singly or in multiple dosage over 24-hour period. For oral administration, the therapeutically effective amount of the active ingredient may be several times greater than that for parenteral administration.

In the practice of the invention the amount of the compound incorporated in the pharmaceutical composition may vary widely. Factors considered when determining the precise amount are well known to those skilled in the art. Examples of such factors include, but are not limited to, age, sex and weight of the subject being treated, intended medical use of the compounds, severity of the disease, the dosage form, route of administration being employed and the frequency with which the composition is to be administered.

Preparation of the Compounds

The compounds of the present invention may be synthesized according to the procedures described in: J. Sterling, et al. U.S. Pat. No. 5,880,157 and M. Bialer et al, Pharm Res. 13:284–289 (1996). The disclosures of these references are incorporated herein by reference in their entirety.

More preferably the compounds of the present invention are synthesized according to the methods outlined below.

The general reaction sequences outlined below are general methods useful for preparing the compounds of the present invention and are not meant to be limiting in scope.

The compounds of formula I as defined in the present invention can be prepared according to reaction scheme I. The process preferably comprises the step of reacting tetramethylcyclopropanecarbonyl chloride (XX) with a suitable amine having the formula (XXI)

wherein $R_1$ and $R_2$ are as defined in formula I.

Reaction scheme I

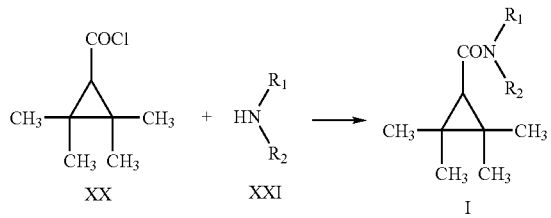

N-methoxy-2,2,3,3-tetramethylcyclopropane carboxamide (compound IV) of the present invention may be prepared by reaction scheme I and the process described below. Additional non limiting examples of compounds which may be synthesized according to reaction scheme I are 2,2,3,3-tetramethylcyclopropanecarbonylamidobenzene-(o,m,p)-sulfonamide (compounds IX–XI).

As used herein the term 'room temperature' refers to a temperature of 20–25° C.

The above process preferably comprises the steps of:

(a) adding tetramethylcyclopropanecarbonyl chloride (XX) dissolved in an inert organic solvent to a stirred solution of a suitable amine having the formula (XXI) defined above; (b) stirring the reaction mixture of step (a) for about 2 hr to about 24 hr, preferably for 2–4 hr at room temperature;

The process further comprises isolating the obtained compounds by means of the following steps:

(c) evaporating the organic solvent and subsequently adding water; (d) extracting the products obtained in step (c) using a suitable organic extraction medium; (e) a step selected from the group consisting of drying, filtering and evaporating the organic medium fraction from step (d); and (f) crystallizing the products using a suitable crystallizing solvent.

The organic solvent of step (a) may be for example dichloromethane, tetrahydrofuran or mixtures thereof.

The amine solution in step (a) preferably includes an anine (occasionally the amine is present as salt such as for example alkoxyl amine hydrochloride) dissolved in organic solvent such as dry dichloromethane. To the amine solution in step (a) further added a basic agent such as triethylamine or pyridine. The basic agent is required in order to increase the yield of the reaction.

Tetramethylcyclopropane carbonyl chloride which is added (drop wise) to the amine solution during the coupling reaction releases hydrochloric acid. This is captured by the basic agent, otherwise it will neutralize the amine and will lower the reaction yield.

In step (c) tetramethylcyclopropanecarbonyl taurine chloride or its analog (XXV) is reacted with a suitable amine (XXVI) such as $NH_3$, a $C_1$–$C_6$alkyl amine, a $C_1$–$C_6$dialkyl amine to obtain compound of formula XXVII.

The $R_3$ and $R_4$ of the amine (XXVI) and amide (XXVII) are the same or different and are independently selected from the group consisting of hydrogen and $C_1$–$C_6$alkyl.

As used herein the term 'taurine analog' refers to a straight or branched —$(CH_2)_n$— alkyl group of the formula $NH_2(CH_2)_nSO_3^-Na^+$ wherein n=1, 3–6.

Taurine refers to the formula $NH_2(CH_2)_nSO_3^-Na^+$ wherein n=2 ($NH_2CH_2CH_2SO_3^-Na^+$).

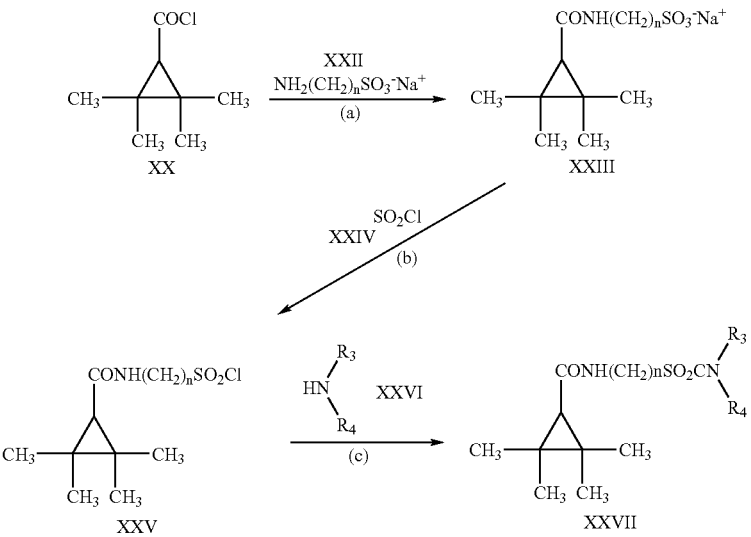

Reaction scheme II

Occasionally it is preferable not to add a basic agent such as pyridine or triethylamine for example as described in reaction scheme III where the urea (or its derivatives) also functions as basic catalyst (basic agent).

The extraction medium of step (d) may be for example ethyl acetate, dichloromethane, chloroform or mixtures thereof, preferably the extraction medium is ethyl acetate.

The organic medium fraction of step (e) may be dried over a drying agent such as $Na_2SO_4$ or $MgSO_4$.

The crystallizing solvent of step (f) may be for example at least one suitable organic solvent, preferably a combination of one to three organic solvents having different polarities for example a mixture of ethyl acetate:petroleum ether, a mixture of dichloromethane:petroleum ether or a mixture of chloroform:hexane. More preferably, the crystallizing solvent of step (f) is a mixture of ethyl acetate and petroleum ether.

The compounds of the invention may be prepared according to reaction scheme II.

In step (a) tetramethylcyclopropanecarbonyl chloride (XX) is reacted with a taurine or its analog having n=1–6 in the formula $NH_2(CH_2)_nSO_3^-Na^+$ (XXII) to obtain tetramethylcyclopropanecarbonyl taurine or its analog (XXIII);

In step (b) tetramethylcyclopropanecarbonyl taurine or its analog (XXIII) is chlorinated using thionyl chloride (XXIV) to obtain tetramethylcyclopropanecarbonyl taurine chloride or its analog (XXV); and The above process may be used to prepare compounds having the formula I:

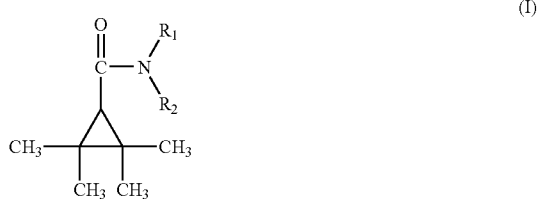

wherein $R_1$ is a hydrogen and $R_2$ may be for example a $C_1$–$C_6$alkyl sulfonamide group or an (N—$C_1$–$C_6$alkyl) $C_1$–$C_6$alkyl sulfonamide group.

Representative compound synthesized by this process is for example N-2,2,3,3-tetramethylcyclopropane carbonyl-taurinamide (compound VIII) described in the present invention.

Compounds of formula I wherein $R_1$ is a $C_1$–$C_6$alkyl, may be similarly synthesized using an N—$C_1$–$C_6$alkyl derivative of the taurine or its analogue (XXII) in step (a).

Preferably step (a) of the above process (reaction scheme II) comprises: (a) adding tetramethylcyclopropanecarbonyl chloride (XX) to a taurine or its analog (XXII) dissolved in a sodium hydroxide aqueous solution, preferably 5–15%, more preferably 10% sodium hydroxide aqueous solution; and (b) stirring the reaction mixture at room temperature, the stirring may be conducted for a period of between 3 and 10 hrs, preferably for 5 hrs.

The process further comprises isolating the obtained compounds by means of the following steps:

(c) evaporating the water; (d) extracting the resulting product by a suitable extraction medium such as boiling ethanol; and (e) filtering off insoluble salts and crystallizing tetramethylcyclopropanecarbonyl taurine or its analog (XXIII) using a suitable solution, the solution may be for example a mixture of ethanol and diethyl ether.

Preferably the chlorinating step (b) of the above process (reaction scheme II) comprises:

chlorinating tetramethylcyclopropanecarbonyl taurine or its analog (XXIII) in dry dichloromethane using thionyl chloride (XX).

Preferably step (c) of the above process (reaction scheme II) comprises:

(a) slowly adding the tetramethylcyclopropanecarbonyl taurine chloride or its analog (XXV) dissolved in dichloromethane to an aqueous solution of the suitable amine (XXVI); and (b) stirring the reaction mixture at room temperature;

The process further comprises isolating the obtained compounds by means of the following steps:

(c) evaporating the organic solvent (dichloromethane); (d) adding water and extracting the resulting products using a suitable organic extraction medium; (e) a step selected from the group consisting of drying, filtering and evaporating the organic fraction; and (f) crystallizing the products using a suitable crystallization solvent.

The amine (XXVI) in the above step (c)(a) may be for example $NH_3$, a $C_1$–$C_6$alkyl amine or a $C_1$–$C_6$dialkyl amine.

Preferably the stirring in step (c)(b) is conducted for 2–5 hrs, preferably for about 2 hrs.

The organic extraction medium in step (d) may be for example chloroform.

The organic medium fraction of step (e) may be dried over a drying agent such as $Na_2SO_4$ or $MgSO_4$.

The crystallization solvent in step (f) may be for example mixture of chloroform and hexane.

Compounds of the invention can be prepared according to reaction scheme III.

In reaction scheme III, 2,2,3,3-tetramethylcyclopropanecarbonyl chloride (XXXI) is reacted with urea or urea derivatives having the formula (XXXII)

wherein $R_1$ is hydrogen or $C_1$–$C_6$ alkyl group, $R_3$ and $R_4$ are the same or different and are independently selected from hydrogen, $C_1$–$C_6$alkyl group, an acyl group having the formula RC(=O)— wherein R is a $C_1$–$C_6$alkyl group, and a keto group having the formula RC(—O)R'— wherein R and R' are $C_1$–$C_6$alkyl groups which may be the same or different.

Representative compound synthesized by this process are for example N-2,2,3,3-tetramethylcyclopropanecarbonyl urea (compound I), 1,1-N,N-dimethyl-2,2,3,3-tetramethyl-cyclopropanecarbonyl urea (compound II) and 1,3-N,N-dimethyl-2,2,3,3-tetramethylcyclopropanecarbonyl urea (compound III).

Reaction Scheme III

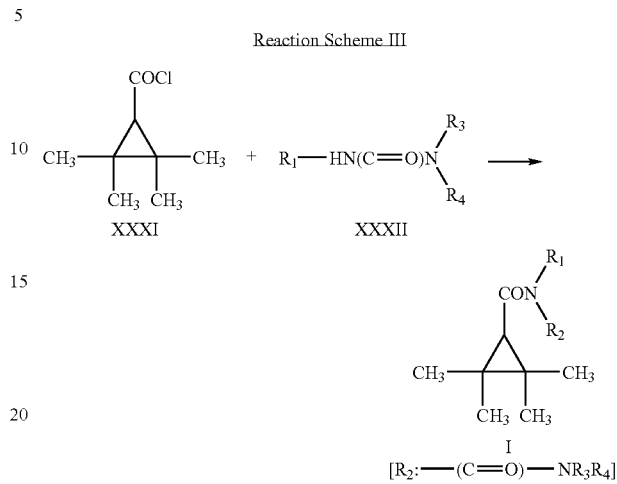

The process in reaction scheme III is carried our by the following steps:

(a) 2,2,3,3-tetramethylcyclopropanecarbonyl chloride (XXXI) dissolved in an inert organic solvent is added to a stirred organic solution of urea or urea derivative (XXXII); and (b) the reaction mixture is stirred for additional 2–24 hrs at a temperature of 25–80° C.

The process further includes isolating the obtained compounds by the following steps:

(c) evaporating the organic solvent; (d) dissolving the obtained products in an inert organic solvent and subsequently washing with water; (e) a step selected from the group consisting of drying, filtering and evaporating the organic fraction from step (d); and (f) crystallizing the products using a suitable organic solvent.

The inert organic solvent of step (a) may be for example an organic polar solvent, an organic non-polar solvent or mixtures thereof, preferably the inert organic solvent of step (a) is an organic polar solvent.

Preferably the organic polar solvent is acetonitrile.

The organic non-polar solvent may be for example benzene or dichloromethane.

The inert organic solvent of step (d) may be for example ethyl acetate, dichloromethane or chloroform.

Preferably the drying in step (e) is performed over a drying agent such as Na2SO4, MgSO4 and mixtures thereof.

The organic solvent of step (f) used for crystallization is preferably a combination of one to three organic solvents having different polarities.

The combination of the organic solvent may be for example ethyl acetate:petroleum ether, dichloromethane: petroleum ether or chloroform:hexane. The ethyl acetate: petroleum ether combination is preferred.

The above reaction scheme III refers to the synthesis of compounds of the present invention wherein $R_1$ is hydrogen or a $C_1$–$C_6$alkyl group and $R_2$ is a member having the structural formula —C(=O)—$(CH_2)_n$—$NR_3R_4$ wherein n=0, $R_3$ and $R_4$ are the same or different and are independently selected from hydrogen, $C_1$–$C_6$alkyl group, an acyl group having the formula RC(=O)—, wherein R is a $C_1$–$C_6$alkyl group, and a keto group having the formula RC(=O)R'—, wherein R and R' are $C_1$–$C_6$ alkyl groups which may be the same or different.

It is appreciated that compounds wherein $R_1$ is hydrogen or a $C_1$–$C_6$ alkyl and $R_2$ is of the structural formula: —C(=O)—(CH$_2$)$_n$—NR$_3$R$_4$ (n=1–6, $R_3$ and $R_4$ are the same as defined above for n=0), may be similarly synthesized using a member having the formula $R_1$HN—(C=O)—(CH$_2$)$_n$—NR$_3$R$_4$ instead of the urea or urea derivative having the formula $R_1$HN—(C=O)—NR$_3$R$_4$ (XXXII) defined above. In the member having the formula $R_1$HN—(C=O)—(CH$_2$)$_n$—NR$_3$R$_4$: n=1–6 and $R_1$, $R_3$ and $R_4$ are the same as defined above for the urea or urea derivative having the formula $R_1$HN—(C=O)—NR$_3$R$_4$ (XXXII)).

Compounds of the invention can be prepared according to reaction scheme IV and by the method described in *Main Group Metal Chemistry* 1997, 20, 151–156, incorporated herein by reference in its entirety.

In step (a) acetazolamide (XL) is hydrolyzed to obtain an acidic salt of (such as hydrochloride of) 5-amino-1,3,4-thiadiazole-2-sulfonamide (XLI) and acetic acid;

In step (b) the acidic salt of (such as hydrochloride of) 5-amino-1,3,4-thiadiazole-2-sulfonamide (XLI) is neutralized till pH 7 to form 5-amino-1,3,4-thiadiazole-2-sulfonamide (XLII);

In step (c) TMC-Cl (XLIII) is reacted with 5-amino-1,3,4-thiadiazole-2-sulfonamide (XLII) to obtain 5-TMCD-1,3,4-thiadiazole-2-sulfonamide (XLIV).

Reaction scheme IV:

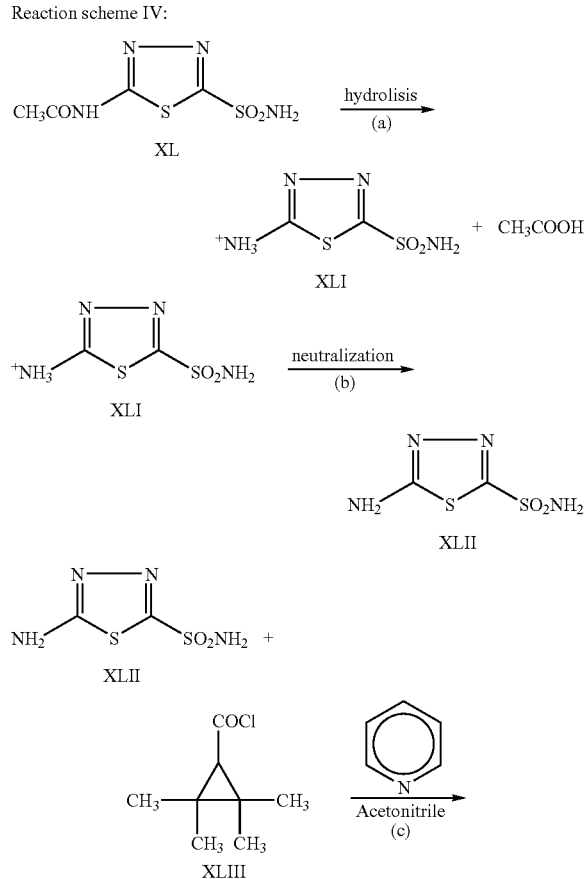

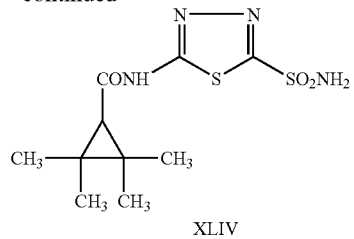

The above process may be used to prepare compounds having the formula I

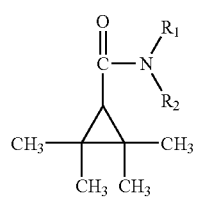

wherein $R_1$ is a hydrogen or a $C_1$–$C_6$ alkyl and $R_2$ is a thiadiazole sulfonamide group.

It is appreciated that when $R_1$ is a $C_1$–$C_6$ alkyl, the $C_1$–$C_6$ alkyl derivative of acetazolamide (XL) is used in step (a).

Preferably step (a) of the above process comprises
(a) dissolving acetazolamide (XL) in a concentrated acidic solution such as hydrochloric solution (preferably at a concentration of 20–35% more preferably 35%) and refluxing (preferably on a water bath, preferably at 50–70° C. and more preferably 60° C.);

step (a) further comprises isolating the obtained compound by means of evaporation of the solvent to obtain a precipitate;

Preferably step (b) of the process of reaction scheme III includes dissolving the precipitate obtained in step (a) (the acidic salt of (such as the hydrochloride of) 5-amino-1,3,4-thiadiazole-2-sulfonamide (XLI)) in water and neutralizing by a basic agent such as NaHCO$_3$ till pH 7 to form 5-amino-1,3,4-thiadiazole-2-sulfonamide (XLII).

Step (b) further includes the step of isolating the obtained product and recrystallizing using a suitable organic solvent such as methanol.

Preferably step (c) of the above process of reaction scheme III comprises
(a) dissolving TMC-Cl (XLIII) in organic solvent preferably dry dichloromethane or dry acetonitrile and adding to 5-amino-1,3,4-thiadiazole-2-sulfonamide (XLII) in the presence of a basic agent preferably pyridine;
(b) leaving the reaction mixture for up to 2 hours at 0°–4° C., preferably under dry conditions;

Step (c) further comprises the isolating the obtained products by means of the following steps:
(c) evaporating the solvent and subsequently adding water and an organic solvent preferably ethyl acetate;
(d) separating the organic phase (e.g. ethyl acetate);
(e) evaporation of the organic phase;

(f) recrystallization of the product obtained in step (e) using a suitable organic solvent, preferably a mixture of ethyl acetate: petroleum ether (preferably at a ratio of 1:3).

It is appreciated that in all the processes described above in reaction schemes I–IV and the examples that follows, the organic solvents used in the reactions (excluding the isolation steps), are preferably dry inert organic solvents, non limiting examples include dry dichloromethane, dry acetonitrile, or dry tetrahydrofuran.

In the isolation steps the organic solvents may be dry or non-dry.

The following Experimental Details are set forth to aid in an understanding of the invention, and are not intended, and should not be construed, to limit in any way the invention set forth in the claims that follow thereafter.

EXAMPLES

Examples 1–4 describe the general synthesis of some of the compounds of the present invention.

Example 1

Synthesis of Compounds Represented by General Formula (I):

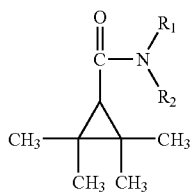

$R_1$ and $R_2$ are as defined in the present invention.

Representative compound synthesize by this process are for example N-methoxy-2,2,3,3-tetramethylcyclopropane carboxamide (compound IV) and 2,2,3,3-tetramethylcyclopropanecarbonylamidobenzene-(o,m,p)-sulfonamide (compounds IX–XI).

Tetramethylcyclopropanecarbonyl chloride (TMC-Cl) dissolved in an inert organic solvent (such as dichloromethane or tetrahydrofuran) was slowly added to a stirred reaction mixture with stirring. The reaction mixture includes an amine dissolved in an organic solvent such as dichloromethane and a basic agent such as triethylamine or pyridine. Occasionally the amine is present as salt such as for example alkoxyl amine hydrochloride. After the addition, the reaction mixture was stirred for about 2–24 hr, preferably for 2–4 hr at room temperature (20–25° C.). The organic solvent was evaporated, water was added and the products were extracted using an organic solvent such as ethyl acetate, dichlorometane or chloroform. The organic fraction was dried over a drying agent such as $Na_2SO_4$ or $MgSO_4$, filtered and evaporated. The product was crystallized using at least one suitable organic solvent, preferably a combination of one to three organic solvents having different polarities for example a mixture of ethyl acetate:petroleum ether, dichloromethane:petroleum ether or chloroform:hexane (preferably a mixture of ethyl acetate:petroleum ether) and its chemical structure was identified by elemental analysis and spectroscopic methods.

Example 2

Synthesis of Compounds Represented by General Formula (I)

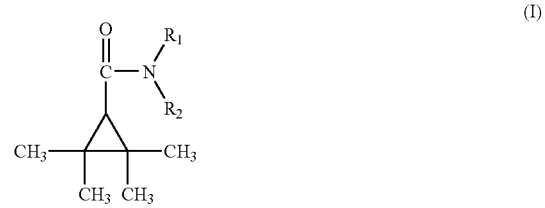

wherein $R_1$ is a hydrogen and $R_2$ is selected from the group consisting of a $C_1$–$C_6$alkyl sulfonamide group or an (N—$C_1$–$C_6$alkyl)$C_1$–$C_6$alkyl sulfonamide group.

Representative compound synthesized by this process is for example N-2,2,3,3-tetramethylcyclopropane carbonyl-taurinamide (compound VIII) described in the present invention.

2,2,3,3-tetramethylcyclopropanecarbonyl taurine (TMC-taurine) is synthesized by adding tetramethylcyclopropanecarbonyl chloride (TMC-chloride) to taurine dissolved in a sodium hydroxide solution, preferably 5–15% NaOH aqueous solution, more preferably 10% NaOH aqueous solution. The reaction mixture is stirred for 3–10 hrs, preferably for 5 hr at room temperature (20–25° C.). The water is evaporated and the product is extracted by boiling ethanol. The insoluble salts are filtered off and TMC-taurine is crystallized using ethanol:diethyl ether solution. TMC-taurine is chlorinated in dry dichloromethane using thionyl chloride and the suitable amides (compound XXVII in reaction scheme II) are synthesized by slowly adding of the TMC-taurine chloride in dichloromethane to an aqueous solution of the corresponding amine (compound XXVI in reaction scheme II). After the addition, the reaction mixture is stirred for 2–5 hr, preferably for 2 hr at room temperature (20–25° C.), the organic solvent is evaporated, water is added and the products are extracted with a suitable organic medium such as chloroform. The organic fraction is dried using a drying agent such as $Na_2SO_4$ or $MgSO_4$, filtered, evaporated and the products are crystallized using chloroform:hexane mixtures to get the desirable product. The chemical structures are identified by elemental analysis and spectroscopic methods.

Example 3

This example describes the synthesis of compounds represented by general formula (I):

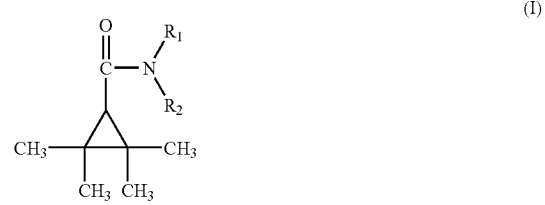

wherein,

R$_1$ is hydrogen or C$_1$–C$_6$ alkyl group and

R$_2$ is urea or urea derivatives having the structural formula:

—C(=O)—NR$_3$R$_4$ wherein R$_3$ and R$_4$ are the same or different and are independently selected from hydrogen, C$_1$–C$_6$alkyl group, an acyl group having the formula RC(=O)—, wherein R is a C$_1$–C$_6$alkyl group, and a keto group having the formula RC(=O)R'—, wherein R and R' are C$_1$–C$_6$alkyl groups which may be the same or different.

2,2,3,3-Tetramethylcyclopropanecarbonyl chloride (TMC-Cl) dissolved in dry inert organic solvent, for example a polar organic solvent such as acetonitrile or an non-polar organic solvent such as benzene or dichloromethane (preferably an organic polar solvent such as acetonitrile) was slowly added to a stirred organic solution of urea or urea derivatives (compound XXXII in reaction scheme III). The organic solution includes an organic solvent for example a polar organic solvent such as acetonitrile, or an non-polar organic solvent such as benzene or dichloromethane, preferably a polar organic solvent such as acetonitrile.

After addition, the reaction mixture was stirred for additional 2–24 hr, preferably 2–3 hr at a temperature of 25–80° C., preferably at 25–40° C. The organic solvent was evaporated under vacuum, the products were dissolved in an inert organic solvent such as ethyl acetate, dichloromethane or chloroform, preferably ethyl acetate and washed with water. The organic fraction was dried over a drying agent such as Na$_2$SO$_4$ or MgSO$_4$, filtered and evaporated. The obtained oil was crystallized using at least one suitable organic solvent, preferably a combination of one to three organic solvents having different polarities for example a mixture of ethyl acetate:petroleum ether, dichloromethane:petroleum ether or chloroform:hexane, preferably a mixture of ethyl acetate: petroleum ether and the product was isolated in a crystalline form. Its chemical structure was identified by elemental analysis and spectroscopic methods.

Example 4

Synthesis of 5-2,2,3,3-tetramethylcyclopropanecarbonylamido-4-methyl-Δ$^2$-1,3,4-thiadiazole-2-sulfonamide 5-imine-4-methyl-Δ$^2$-1,3,4-thiadiazole-2-sulfomamide (methazol) and a basic agent such as pyridine or triethylamine (preferably triethylamine) are dissolved in an organic solvent preferably anhydrous acetonitrile (or dry dichloromethane). TMC-chloride dissolved in an organic solvent preferably anhydrous acetonitrile (or dry dichlorometane) is slowly added to the organic solution including the metazol and the basic agent. The reaction is stirred at room temperature (20° C.–25° C.) for 3–6 hours. The solvent is evaporated (e.g. in vacuum). The residue obtained after evaporation is dissolved in cold water (preferably at a temperature of about 4° C.) and the precipitate product is filtered and recrystallized from an organic solvent preferably acetonitrile. (approximate yield 75%).

As used herein methazol refers to

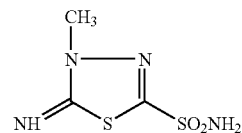

Example 5

Synthesis of N-(2,2,3,3-tetramethylcyclopropanecarbonyl)urea (TMC-Urea) (compound I)

TMC-Urea (compound I) was prepared in a manner analogous to that described in Example 3 and reaction scheme III.

2,2,3,3-Tetramethylcyclopropanecarbonyl chloride (TMC-Cl) (1.25 g, 8 mmole) dissolved in dry boiling acetonitrile was slowly added to stirred acetonitrile solution of urea (1.17 g, 19.5 mmole). After addition, the reaction mixture was stirred for additional 2 hr at 40° C. The organic solvent was evaporated under vacuum, the products were dissolved in 30 ml ethyl acetate and washed with 10 ml water. The organic fraction was dried over Na$_2$SO$_4$, filtered and evaporated under vacuum. The obtained oil was crystallized using a mixture of solvents, ethyl acetate and petroleum ether (2:3), and the product (TMC-Urea) was isolated in crystalline form to afford 900 mg (75% yield). Its chemical structure was identified by elemental analysis and spectroscopic methods.

Results of Chemical Structure and Identification Methods of TMC-Urea:

$^1$H NMR (CDCl$_3$; 300 MHz): 8.2 (d, br., 2H), 5.2 (s, br., 1H), 1.6 (s, 1H), 1.3 (s, 6H), 1.2 (s, 6H) ppm. MS(m/z): 184 (1.06), 169 (35.64), 126 (38.57), 97 (52.50), 83 (37.22), 55 (100). MP (melting point): 194° C. Elemental Analysis: Found (Calculated): C, 58.73% (58.67%), H, 8.75% (8.75%), N, 15.50% (15.21%). Crystals: White flakes-like crystals Example 6

Synthesis of 1,1-N,N-dimethyl-2,2,3,3-tetramethyl-cyclopropanecarbonyl urea (compound II)

The synthesis of 1,1-N,N-dimethyl-2,2,3,3,-tetramethyl-cyclopropanecarbonyl urea was identical to the synthesis of TMC-Urea described above (in example 5) with the modification that in this reaction 1,1-dimethyl urea was used instead of urea.

The product (1,1-N,N-dimethyl-2,2,3,3,-tetramethylcyclopropanecarbonyl urea) was isolated in crystalline form to afford 1.5 g (90% yield). Its chemical structure was identified by elemental analysis and spectroscopic methods.

Results of the Chemical Structure and Identification of 1,1-N,N-dimethyl-2,2,3,3,-tetramethylcyclopropanecarbonyl Urea $^1$H NMR(CDCl$_3$; 300 MHz): 1.22 (d, J=13.5, 12H), 1.81 (s, 1H), 2.97 (s, 6H), 7.56 (br s, 1H). MS(m/z): 213 (M$^+$+1, 3), 125 (32), 109 (41), 96 (70), 82 (68), 55 (100). MP (melting point): 105° C. Elemental Analysis: Found (Calculated): C, 62.17 (62.24); H, 9.52 (9.50); N, 13.13 (13.19). Crystals: White crystals.

Example 7

Synthesis of 1,3-N,N-dimethyl-2,2,3,3-tetramethyl-cyclopropanecarbonyl urea (compound III)

The synthesis of 1,3-N,N-dimethyl-2,2,3,3-tetramethyl-cyclopropanecarbonyl urea was identical to the synthesis of TMC-Urea described above (in example 5) with the modification that in this reaction 1,3-dimethyl urea was used instead of urea.

The product (1,3-N,N-dimethyl-2,2,3,3-tetramethylcyclopropanecarbonyl urea) was isolated in crystalline form to afford 1.5 g (90% yield). Its chemical structure was identified by elemental analysis and spectroscopic methods.

Results of the Chemical Structure and Identification of 1,3-N,N-dimethyl-2,2,3,3-tetramethylcyclopropanecarbonyl Urea $^1$H NMR(CDCl$_3$; 300 MHz): 1.20 (d, J=7.5, 12H), 1.28 (s, 1H), 2.83–2.87 (m, 3H), 3.29 (q, J=0.6, 3H), 9.13 (brs, 1H). MS(m/z): 212 (M$^+$, 0.2), 128 (59), 96 (100), 83 (20), 69 (12), 55 (63). MP (melting point): 55–56° C. Elemental Analysis: Found (Calculated): C, 62.11 (62.24); H, 9.43 (9.50); N, 13.24 (13.19). Crystals: White crystals.

Example 8

Synthesis of N-methoxy-2,2,3,3,-tetramethylcyclopropane carboxamide (N-methoxy TMCD) (compound V)

N-methoxy TMCD was synthesized in a manner analogous to that described in example 1 and reaction sheme I.

Tetramethylcyclopropanecarbonyl chloride (TMC-Cl) (4 g; 25 mmol) dissolved in 20 ml of dry dichloromethane was slowly added to a stirred and dry dichloromethane solution of methoxylamine hydrochloride (2.5 g; 30 mmol) and triethylamine (6.3 g; 50 mmol). After the addition, the reaction mixture was stirred for 2 hr at room temperature. Dichloromethane was evaporated under vacuum, 10 ml of water was added and the products were extracted using 30 ml of ethyl acetate. The organic fraction was dried over MgSO$_4$, filtered and evaporated under vacuum. The product was crystallized using 20 ml ethyl acetate and 30 ml petroleum ether to afford 3 g (75% yield) and its chemical structure was identified by elemental analysis and spectroscopic methods.

Results of the Chemical Structure and Identification for N-methoxy-2,2,3,3,-tetramethylcyclopropane Carboxamide $^1$H NMR(CDCl$_3$; 300 MHz): 1.18 (s, 6H), 1.28 (s, 7H), 3.74 (s, 3H), 7.84 (br s, 1H). MS(m/z): 171 (M$^+$, 0.6), 156 (21), 125 (98), 97(17), 83 (22), 55 (100). MP (melting point): 78° C. Elemental Analysis: Found (Calculated): C, 63.22% (63.13%); H, 9.98% (10.01%); N, 8.24% (8.18%). Crystals: White wool-like material.

Example 9

Synthesis of 5-(tetramethylcyclopropanecarbonylamido)-1,3,4-thiadiazole-2-sulfonamide (compound VI)

Compound VI was synthesized in a manner analogous to that described in reaction scheme IV.

(i) procedure for the synthesis of 5-amino-1,3,4-thiadiazole-2-sulfonamide 22.2 gr of acetazolamide, was dissolved in 100 ml concentrated HCl solution (35%) and refluxed on a water bath (60° C.) for two hours.

The solvent was evaporated and the 5-amino-1,3,4-thiadiazole-2-sulfonamide was obtained as a white precipitate. This was dissolved in 50 ml of water and neutralized with NaHCO$_3$ till pH 7. The product was recrystallized from methanol to afford 12 g (yield of 54%).

White crystals. M.P. 230–231° C.

(ii) procedure for the synthesis of 5-tetramethylcyclopropanecarbonyl amido-1,3,4-thiadiazole-2-sulfonamide (compound VI)

4 gr of TMC-Cl dissolved in 52 ml dry dichloromethane were added to 4.5 gr of 5-amino-1,3,4-thiadiazole-2-sulfonamide, and 5.2 ml of pyridine in a round bottomed flask. The reaction mixture was held in 4° under dry conditions for 1.5 hrs. The solution was evaporated twice under vacuum, after adding water (50 ml) and the residue was extracted with 150 ml of ethyl acetate. The organic phase was separated and evaporated under vacuum. The product was recrystalized with ethyl acetate:petroleum ether (1:3) to afford 3.2 g (yield 66%).

White crystals. M.P.: 239° C. $^1$H NMR (300 MHz, DMSO): 1.189–1.218 (d, 12H), 1.543 (s, 1H), 8.265 (br,s 2H). Anal. (C$_{10}$H$_{16}$N$_4$O$_3$S$_2$) C, H, N.

Example 10

Biological Activity

The compounds of the present invention were tested for their ability to protect against chemically and electrically induced convulsions, in two models of epilepsy in mice and rats. The first model, the maximal electroshock seizure test (MES), is used to show efficacy for antiepileptic agents against partial and generalized seizure type epilepsy, the common epilepsy among therapy resistant epileptic patients. The second model, the subcutaneous metrazole test (scMet) measures seizure threshold and is a standard screening procedure to show efficacy for agents against seizure threshold and absence seizures. These models are described in White H S et al, General principles-Discovery and preclinical development of antiepileptic drugs, in: Antiepileptic Drugs, 5$^{th}$ edition, R H Levy, R H Mattson, B S Meldrum, E Perucca (eds), Lippincott William & Wilkins, Philadelphia 2002, pp. 36–48.

The biological activity studies of the present invention were conducted according to the protocol described therein (White H S et al, General principles—Discovery and preclinical development of antiepileptic drugs, in: Antiepileptic Drugs, 5$^{th}$ edition, R H Levy, R H Mattson, B S Meldrum, E Perucca (eds), Lippincott William & Wilkins, Philadelphia 2002, pp. 36–48).

As used herein "p.o' refers to oral administration.

As used herein "ip" refers to intraperitoneal administration.

As used herein "sc" refers to subcutaneous administration.

N-2,2,3,3-tetramethylcyclopropanecarbonyl urea (compound I) showed an anticonvulsant activity in rat-MES model. The ED50 (median effective dose) in the MES model following oral administration to rats was 29.4 mg/kg with a 95% confidence interval (CI) of 17.6 to 47.4 mg/kg. For comparison, N-methyl 2,2,3,3-tetramethylcyclopropane carboxamide (M-TMCD) had in rat-MES ED50 of 82 mg/kg with CI of 64 to 103 mg/kg [N. Isoherranen et al, Epilepsia, 43(2): 115–126, 2002] and N-2,2,3,3-tetramethylcyclopropyl carbonyl-glycinamide that had an ED50 of 82 mg/kg with CI of 61 to 103 mg/kg (Bialer et al., Pharm. Res. 13 (2):284–289, 1996).

Compound I also showed an anticonvulsant activity in rats in the scMet test. The ED50 (rats, p.o.) in the scMet model was 91.8 mg/kg with a 95% confidence interval (CI) of 50–151 mg/kg. For comparison, N-2,2,3,3-tetramethylcyclopropyl carbonyl-glycinamide was in active at a dose of 250 mg/kg (ED50>250 mg/kg) [Bialer et al., Pharm. Res. 13 (2):284–289, 1996].

Table 1 describes the ED50 biological response of compound I in the MES and scMET test.

TABLE 1

ED50 biological response

| Test | Dose (mg/kg) | N/F[*] |
|---|---|---|
| MES | 10 | 0/8 |
| MES | 20 | 4/8 |
| MES | 40 | 5/8 |
| MES | 80 | 7/8 |
| scMET | 25 | 1/8 |
| scMET | 50 | 3/8 |
| scMET | 100 | 3/8 |
| scMET | 200 | 6/8 |
| scMET | 400 | 8/8 |

[*]N/F represents the fraction of rats responded at a specific dose.

N-2,2,3,3-tetramethylcyclopropanecarbonyl urea (Compound I) showed an anticonvulsant activity in mice-MES model. The ED50 in the MES model in mice following ip administration was 90 mg/kg with a 95% confidence interval (CI) of 83 to 96 mg/kg. For comparison, N-methyl 2,2,3,3-tetramethylcyclopropane carboxamide (M-TMCD) had in mice-MES ED50 of 99 mg/kg with CI of 88 to 109 mg/kg [N. Isoherranen et al, Epilepsia, 43(2): 115–126, 2002] and N-2,2,3,3-tetramethylcyclopropyl carbonyl-glycinamide that had an ED50 of 173 mg/kg with CI values of 149 and 202 mg/kg (Bialer et al., Pharm. Res. 13 (2):284–289, 1996).

Compound I also showed an anticonvulsant activity in mice in the scMet test. The ED50 (mice, ip) in the scMet model was 125 mg/kg with a 95% confidence interval (CI) of 93–176 mg/kg.

1,1-N,N-dimethyl-2,2,3,3-tetramethylcyclopropanecarbonyl urea (1,1-N,N-dimethyl TMC Urea) showed an anticonvulsant activity in rat-MES model. The ED50 in the MES model following oral administration to rats was 87 mg/kg with a CI values of 32–211 mg/kg and no neurotoxicity was shown at doses up to 500 mg/kg.

N-methoxy-2,2,3,3-tetramethylcyclopropane carboxamide (compound V) showed an anticonvulsant activity in rat-scMet model. The ED50 in the scMet model following oral administration to rats was 35 mg/kg with CI of 16–54 mg/kg.

Compound V showed an anticonvulsant activity in mice-MES model and Mice-scMET model. The ED50 (mice, ip) in the MES model was 115 mg/kg with CI of 103–126 mg/kg. The ED50 (mice, ip) in the scMet model was 74 mg/kg with CI of 64–83 mg/kg.

5-2,2,3,3-tetramethylcyclopropanecarbonylamido-1,3,4-thiadiazole-2-sulfonamide (TMC-thidiazole—Compound VI) showed an anticonvulsant activity in mice-MES model. The ED50 in the MES model in mice following ip administration was 16 mg/kg with a CI of 14–22 mg/kg.

Neurotoxicity

Neurotoxicity of the claimed agents was assessed in mice (ip. administration) in the rotorod ataxia test and in rats (po. administration) in the gait and stance test which assesses minimal neurotoxicity. The term qauntitating the neurotoxicity is the median neurological toxic dose (TD50). In some of the species the TD50 was determined to be above a certain level, indicating a lower neurotoxicity than specified.

The protective index (PI) is defined as the ratio of TD50 and ED50 (PI=TD50/ED50). The PI is used to show a useful separation between neurotoxicity and antiepileptic activity. The larger the PI, the better the separation between neurotoxicity and efficacious doses.

The neurotixicity studies were conducted according to the protocol described in White H S et al, General principles—Discovery and preclinical development of antiepileptic drugs, in: Antiepileptic Drugs, 5$^{th}$ edition, R H Levy, R H Mattson, B S Meldrum, E Perucca (eds), Lippincott William & Wilkins, Philadelphia 2002, pp. 36–48.

The TD50 of compound I (N-2,2,3,3-tetramethylcyclopropanecarbonyl urea (TMC-urea)) was 538 mg/kg following oral administration to rats. For comparison N-methyl 2,2,3,3-tetramethylcyclopropane carboxamide (M-TMCD) had an neurotoxic dose (TD50) of 163 mg/kg (CI=138–179 mg/kg) [N. Isoherranen et al, Epilepsy, 43(2): 115–126, 2002]. VPA had a TD50 value of 280 mg/kg. N-2,2,3,3-tetramethylcyclopropyl carbonyl-glycinamide (TMC glycinamide) had an TD50 of above 500 mg/kg (Bialer et al., Pharm. Res. 13 (2):284–289, 1996).

Thus, the protective index or safety of margin TD50/ED50 is 2 for M-TMCD, 0.6 for VPA, >6.1 for TMC glycinamide, and 18.5 for compound I.

The TD50 (mice, ip) of N-Methoxy-2,2,3,3-tetramethylcyclopropane carboxamide (compound V) was 166 mg/kg with a CI of 152–183 mg/kg.

Taken together, these results suggest that the novel compounds of the present invention have unexpected potential as a drug for the treatment of epilepsy.

The results show that N-2,2,3,3-tetramethylcyclopropanecarbonyl urea and its derivatives such as 1,1-N,N-dimethyl-2,2,3,3-tetramethylcyclopropanecarbonyl urea; N-methoxy-2,2,3,3-tetramethylcyclopropane carboxamide; and 5-2,2,3,3-tetramethylcyclopropanecarbonylamido-1,3,4-thiadiazole-2-sulfonamide;

are preferred because of their high anti-epileptic potency.

N-2,2,3,3-tetramethylcyclopropanecarbonyl urea (Compound I) is more preferred compared to other cyclopropyl analogues of VPA because of its high potency and wide margin of safety.

Example 11

The objective of this study is to asses the antiallodynic activity of TMC-Urea (compound I) in the rat spinal nerve ligation (SNL) model for neuropathic pain.

Materials and Method

Animals and Experimental Setup

Experiments were performed on male Sprague-Dawley rats (Harlan laboratories, Jerusalem, Israel) weighing 175–200 g. The mechanical sensitivity (tactile allodynia) of the foot was quantified by the occurrence of foot withdrawal in response to normally innocuous mechanical stimuli using nine different von Frey filaments (VFF) ranging from 0.6 to 26 g. The rats were placed on a metal mesh floor covered with a transparent plastic dome and a period of acclimatization was allowed prior to testing. VFF were applied from underneath the mesh floor to the plantar surface of the foot. Each trial consisted of repeated applications of each of the VFFs in an ascending order for 5 times, each for a period of 1 s. If the rat withdrew the foot at least 3 times out of 5 at a specific VFF no further ascending filaments were tested and this filament was considered as a withdrawal threshold (response). Mechanical stimulus trials with the series of ascending VFF were repeated 2 times for a given time point. The repeated measurements were averaged and taken as the paw withdrawal threshold on a given time point.

Rats that did not withdraw the foot to mechanical stimulus (von Frey filaments) of 15 g and above for 2 consecutive days (−2 and −1) were included in the study. For drug testing, the effect on neuropathic pain was measured 5–6 days following operation. Rats responding to mechanical stimuli of 10 g or less (in the operated leg) were eligible for the study.

Surgical Procedure

The procedure of ligation and cut of the spinal nerves for induction of neuropathic pain was performed as previously described by Sheen and Chung (Sheen, K. and Chung, J. M., Signs of neuropathic pain depend on signals from injured nerve fibers in a rat model, *Brain Research* 610: 62–68 (1993)). Briefly, under ketamine-xylazine anaesthesia rats were placed in a prone position and the left paraspinal muscles were separated from spinous processes at the L4-S2 level. Part of the L6 transverse process was removed and the L4–L6 spinal nerves were identified. The L5–L6 spinal nerves were isolated and tightly ligated and cut, distal to the dorsal root ganglion and proximal to the formation of the sciatic nerve. Following complete homeostasis the wound was sutured.

Pharmacologocal Treatments

For all the studies, appropriate amounts of the tested compound were suspended in 0.5% methylcellulose to a volume of 4 mL/kg body weight. TMC-Urea and methylcellulose (MC, vehicle) were administered intraperitoneally (i.p) to rats at postoperative days 7, 14 and 21 in a double blind randomized crossover manner.

Determination of the Median Effective Dose

Rats that obtained threshold of 15 g and above, back to pre-operation baseline, were regarded free of tactile allodynia. Groups of seven to ten animals were administered with increasing doses of TMC-Urea until at least four points were established between the dose level that did not protect any of the animals and the dose level that protected 100% of the animals.

Median effective dose ($ED_{50}$) and its 95% confidence intervals were calculated using the pharmacodynamic software package WinNonlin, version 4.0.1 (SCI Software, Lexington, Ky., U.S.A.).

Statistical Analysis

Threshold data from VFF testing are presented as actual threshold (absolute) in grams and as percent of absolute responders.

For statistical analyses the nonparametric two-tailed Mann-Whitney U was used. A p value less than 0.05 was considered significant.

Results

Following the surgical procedure, all rats that entered into this study displayed a significant (p<0.05, data not shown) decrease in the mechanical stimulus necessary to evoke a brisk withdrawal response of the injured hindpaw in response to VFF stimulation, compared to pre-surgical response. The contralateral (unoperated) side failed to respond to any filament of 15 g or above.

Effects of TMC-Urea on Tactile Allodynia

Following i.p administration, TMC-Urea decreased tactile allodynia in a dose-dependent manner, with a significant reduction in the response occurring at 120 to 240 min at 120–240 mg/kg (FIG. 1). The $ED_{50}$ value, at 120 min post-dose, was 171 mg/kg, CI of 127–215 mg/kg. TMC-Urea at doses of 120 and 240 mg/kg possessed superiority over vehicle from 30 up to 240 min post-dosing (p≦0.05) with exceptions of 30 min at 120 mg/kg (Table 1).

TABLE 1

| | Allodynic response (number of rats responded/total number of rats) | | | | | |
|---|---|---|---|---|---|---|
| | Time | | | | | |
| Comp (mg/kg) | 30 min | 60 min | 120 min | 180 min | 240 min | Total responders |
| TMC-Urea | | | | | | |
| 20 mg/kg ip | 0/9 | 0/9 | 0/9 | 0/9 | 0/9 | 0/9 |
| 60 mg/kg ip | 0/9 | 0/9 | 0/9 | 0/9 | 0/9 | 0/9 |
| 120 mg/kg ip | 0/9 | 1/9 ** | 3/9 *** | 3/9 * | 3/9 * | 3/9 |
| 180 mg/kg ip | 0/7 | 1/7 | 3/7 | 3/7 | 3/7 | 3/7 |
| 240 mg/kg ip | 0/10 * | 2/10 *** | 8/10 *** | 8/10 *** | 8/10 *** | 9/10 |

The statistical analysis was calculated by two-tailed Mann-Whitney test. Significance of threshold from vehicle control at p<0.05, 0.01 and 0.001 levels are indicated by single, double and triple asterisks (*), respectively.

Figure 2:
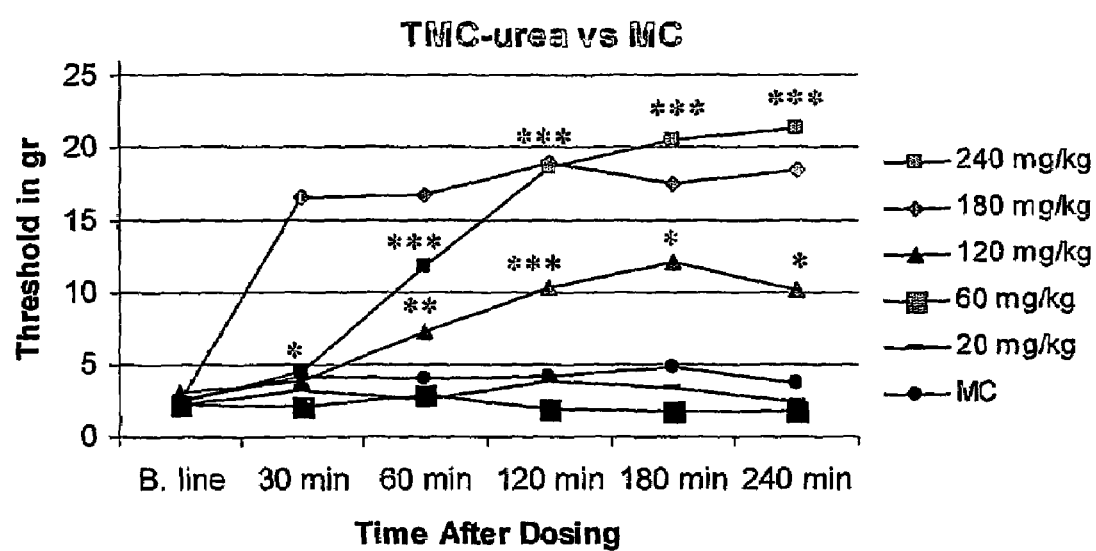
FIG. 2 illustrates the allodynic response presented as the actual threshold (absolute) in grams in the VFF testing.

FIG. 2 describes the time course of the change in threshold following administration of 20, 60, 120, 180 and 240 mg/kg of TMC-urea, i.p. The experiments performed with TMC-urea dissolved in the vehicle (methyl cellulose) included 5 repetitions using 7–10 rats for each experiment. Significance of threshold from vehicle control at p<0.05, 0.01 and 0.001 levels are indicated by single, double and triple asterisks (*), respectively.

While this invention has been shown and described with reference to preferred embodiments thereof, it will be understood by those skilled in the art that many alternatives, modifications and variations may be made thereto without departing from the spirit and scope of the invention. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

What is claimed is:

1. A 2,2,3,3-tetramethylcyclopropane carboxamide derivative compound of formula I:

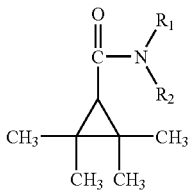

including enantiomers, hydrates, solvates and pharmaceutically acceptable salts thereof
wherein,
$R_1$ is hydrogen or $C_1$–$C_6$ alkyl group and
$R_2$ is selected from the group consisting of:
(a) a member having the structural formula:

wherein n=0–6, $R_3$ and $R_4$ are the same or different and are independently selected from the group consisting of hydrogen, $C_1$–$C_6$alkyl group, an acyl group having the formula RC(=O)—, wherein R is a $C_1$–$C_6$alkyl group, and a keto group having the formula RC(=O)R'—, wherein R and R' are $C_1$–$C_6$alkyl groups which may be the same or different;
(b) a $C_1$–$C_6$alkyl sulfonamide group;
(c) an (N—$C_1$–$C_6$alkyl)$C_1$–$C_6$alkyl sulfonamide group;
(d) an aryl sulfonamide group;
(e) a thiadiazole sulfonamide group;
(f) a $C_1$–$C_6$alkyl-thiadiazole sulfonamide group;
(g) an (N—$C_1$–$C_6$alkyl)aryl sulfonamide group;
(h) an (N—$C_1$–$C_6$alkyl)$C_1$–$C_6$alkyl aryl sulfonamide group;
(i) an (N—$C_1$–$C_6$alkyl)thiadiazole sulfonamide group;
(j) an (N—$C_1$–$C_6$alkyl)$C_1$–$C_6$alkyl-thiadiazole sulfonamide group; and
(k) a $C_1$–$C_6$alkoxy group.

2. The derivative compound of claim 1 wherein $R_1$ is hydrogen.

3. A 2,2,3,3-tetramethylcyclopropane carboxamide derivative compound of formula I:

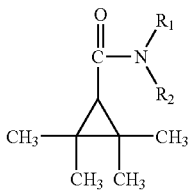

including enantiomers, hydrates, solvates and pharmaceutically acceptable salts thereof
wherein,
$R_1$ is $C_1$–$C_6$ alkyl group and
$R_2$ is selected from the group consisting of:
(a) a member having the structural formula:

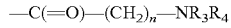

wherein n=0–6, $R_3$ and $R_4$ are the same or different and independently selected from the group consisting of hydrogen, $C_1$–$C_6$alkyl group, an acyl group having the formula RC(=O)—, wherein R is a $C_1$–$C_6$alkyl group, and a keto group having the formula RC(=O)R'—, wherein R and R' are $C_1$–$C_6$alkyl groups which may be the same or different;
(b) a $C_1$–$C_6$alkyl sulfonamide group;
(c) an (N—$C_1$–$C_6$alkyl)$C_1$–$C_6$alkyl sulfonamide group;
(d) an aryl sulfonamide group;
(e) a $C_2$–$C_6$alkyl aryl sulfonamide group;
(f) a thiadiazole sulfonamide group;
(g) a $C_1$–$C_6$alkyl-thiadiazole sulfonamide group;
(h) an (N—$C_1$–$C_6$alkyl)aryl sulfonamide group;
(i) an (N—$C_1$–$C_6$alkyl)$C_1$–$C_6$alkyl aryl sulfonamide group;
(j) an (N—$C_1$–$C_6$alkyl)thiadiazole sulfonamide group;
(k) an (N—$C_1$–$C_6$alkyl)$C_1$–$C_6$alkyl-thiadiazole sulfonamide group; and
(l) a $C_1$–$C_6$alkoxy group.

4. The derivative compound of claim 1 wherein any alkyl group or alkoxy group of $R_2$ is a straight or branched chain.

5. The derivative compound of claim 1 wherein n in the structural formula —C(=O)—(CH$_2$)$_n$—NR$_3$R$_4$ is zero.

6. The derivative compound of claim 1 wherein $R_1$ is hydrogen or $C_1$–$C_6$ alkyl group and $R_2$ is a member having the structure formula:

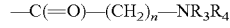

wherein n=0, and $R_3$ and $R_4$ are the same or different and are independently selected from the group consisting of hydrogen and $C_1$—$C_6$ alkyl group.

7. The derivative compound of claim 6 wherein $R_1$, $R_3$ and $R_4$ are hydrogen.

8. The derivative compound of claim 6 wherein at least one of said $R_1$, $R_3$ or $R_4$ is a methyl.

9. The derivative compound of claim 1 wherein said $R_2$ is $C_1$–$C_6$alkoxy group.

10. The derivative compound of claim 1 wherein said $R_1$ is hydrogen and said $R_2$ is $C_1$–$C_6$alkoxy group.

11. The derivative compound of claim 9 or 10 wherein said $C_1$–$C_6$alkoxy group is methoxy.

12. The derivative compound of claim 1 wherein $R_2$ is thiadiazole sulfonamide group.

13. The derivative compound of claim 1 wherein said $R_1$ is hydrogen and said $R_2$ is thiadiazole sulfonamide group.

14. The derivative compound of claim 1 wherein said $R_2$ is aryl sulfonamide group.

15. The derivative compound of claim 1 wherein said $R_1$ is hydrogen and said $R_2$ is aryl sulfonamide group.

16. The derivative compound of claims 14 or 15 wherein said aryl sulfonamide group is a phenyl sulfonamide group.

17. The derivative compound of claim 1, being selected from the group consisting of:
N-2,2,3,3-tetramethylcyclopropanecarbonyl urea;
1,1-N,N-dimethyl-2,2,3,3-tetramethylcyclopropanecarbonyl urea;
1,3-N,N-dimethyl-2,2,3,3-tetramethylcyclopropanecarbonyl urea;
N-acetyl-2,2,3,3-tetramethylcyclopropanecarbonyl urea;
N-methoxy-2,2,3,3-tetramethylcyclopropane carboxamide;
5-2,2,3,3-tetramethylcyclopropanecarbonylamido-1,3,4-thiadiazole-2-sulfonamide;
5-2,2,3,3tetramethylcyclopropanecarbonylamido-4-methyl-Δ$^2$-1,3,4-thiadiazole-2-sulfonamide;
N-2,2,3,3-tetramethylcyclopropanecarbonyl-taurinamide;
2,2,3,3-tetramethylcyclopropanecarbonylamidobenzene-o-sulfonamide;
2,2,3,3-tetramethylcyclopropanecarbonylamidobenzene-m-sulfonamide; and 2,2,3,3-tetramethylcyclopropanecarbonylamidobenzene-p-sulfonamide.

18. A pharmaceutical composition comprising as an active ingredient a therapeutically effective amount of at least one compound of formula I:

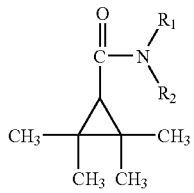

including enantiomers, hydrates, solvates and pharmaceutically acceptable salts thereof
wherein,
$R_1$ is hydrogen or $C_1$–$C_6$ alkyl group and
$R_2$ is selected from the group consisting of:
(a) a member having the structural formula:

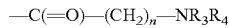

—C(=O)—(CH$_2$)$_n$—NR$_3$R$_4$ wherein n=0–6, $R_3$ and $R_4$ are the same or different and are independently selected from the group consisting of hydrogen, $C_1$–$C_6$alkyl group, an acyl group having the formula RC(=O)—, wherein R is a $C_1$–$C_6$alkyl group, and a keto group having the formula RC(=O)R'—, wherein R and R' are $C_1$–$C_6$alkyl groups which may be the same or different;
(b) a $C_1$–$C_6$alkyl sulfonamide group;
(c) an (N—$C_1$–$C_6$alkyl)$C_1$–$C_6$alkyl sulfonamide group;
(d) an aryl sulfonamide group;
(e) a thiadiazole sulfonamide group;
(f) a $C_1$–$C_6$alkyl-thiadiazole sulfonamide group;
(g) an (N—$C_1$–$C_6$alkyl)aryl sulfonamide group;
(h) an (N—$C_1$–$C_6$alkyl)$C_1$–$C_6$alkyl aryl sulfonamide group;
(i) an (N—$C_1$–$C_6$alkyl)thiadiazole sulfonamide group;
(j) an (N—$C_1$–$C_6$alkyl)$C_1$–$C_6$alkyl-thiadiazole sulfonamide group; and
(k) a $C_1$–$C_6$alkoxy group and a pharmaceutically acceptable carrier.

19. The pharmaceutical composition of claim 18 wherein the route of administration of said composition is oral, parenteral, inhalation, topical, transdermal, intranasal or rectal.

20. The pharmaceutical composition of claim 19 wherein said parenteral route of administration is intravenous, intramuscular, intraperitoneal or subcutaneous administration.

21. A pharmaceutical composition according to claim 18 for the treatment of any of psychotic disorders, neurodegenerative diseases, epilepsy and pain.

22. A method of treating or ameliorating a medical condition selected from psychotic disorders, neurodegenerative diseases, epilepsy and pain, in a mammal in need of such treatment comprising administering to the mammal an effective amount of a compound of formula I:

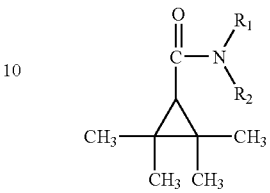

including enantiomers, hydrates, solvates and pharmaceutically acceptable salts thereof
wherein,
$R_1$ is hydrogen or $C_1$–$C_6$ alkyl group and
$R_2$ is selected from the group consisting of:
(a) a member having the structural formula:

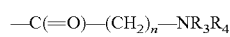

—C(=O)—(CH$_2$)$_n$—NR$_3$R$_4$ wherein n=0–6, $R_3$ and $R_4$ are the same or different and are independently selected from the group consisting of hydrogen, $C_1$–$C_6$alkyl group, an acyl group having the formula RC(=O)—, wherein R is a $C_1$–$C_6$alkyl group, and a keto group having the formula RC(=O)R'—, wherein R and R' are $C_1$–$C_6$alkyl groups which may be the same or different;
(b) a $C_1$–$C_6$alkyl sulfonamide group;
(c) an (N—$C_1$–$C_6$alkyl)$C_1$–$C_6$alkyl sulfonamide group;
(d) an aryl sulfonamide group;
(e) a $C_2$–$C_6$alkyl aryl sulfonamide group;
(f) a thiadiazole sulfonamide group;
(g) a $C_1$–$C_6$alkyl-thiadiazole sulfonamide group;
(h) an (N—$C_1$–$C_6$alkyl)aryl sulfonamide group;
(i) an (N—$C_1$–$C_6$alkyl)$C_1$–$C_6$alkyl aryl sulfonamide group;
(j) an (N—$C_1$–$C_6$alkyl)thiadiazole sulfonamide group;
(k) an (N—$C_1$–$C_6$alkyl)$C_1$–$C_6$alkyl-thiadiazole sulfonamide group; and
(l) a $C_1$–$C_6$alkoxy group.

23. The method of claim 22 wherein said psychotic disorder is schizophrenia, anxiety, depression or bipolar disorder.

24. The method of claim 22 wherein said pain is neuropathic pain, chronic pain, headaches and migraine.

25. The method of claim 22 wherein said mammal is a human.

* * * * *